(12) United States Patent
Fujise et al.

(10) Patent No.: US 7,101,852 B2
(45) Date of Patent: Sep. 5, 2006

(54) COMPOSITION AND METHOD FOR TREATMENT AND PREVENTION OF RESTENOSIS

(75) Inventors: Kenichi Fujise, Houston, TX (US); Zakar H. Mnjoyan, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 305 days.

(21) Appl. No.: 10/448,664

(22) Filed: May 30, 2003

(65) Prior Publication Data

US 2004/0242470 A1 Dec. 2, 2004

(51) Int. Cl.
*A61K 38/17* (2006.01)
(52) U.S. Cl. ...................................................... 514/12
(58) Field of Classification Search ...................... None
See application file for complete search history.

(56) References Cited

U.S. PATENT DOCUMENTS 5,980,566 A * 11/1999 Alt et al. .................... 623/23.7
6,420,121 B1 * 7/2002 Nelson et al. ............... 435/7.1

FOREIGN PATENT DOCUMENTS

WO        WO 00/11950      *   3/2000

OTHER PUBLICATIONS

Schlimgen AK, Helms JA, Vogel H, et al. Neuronal pentraxin, a secreted protein with homology to acute phase proteins of the immune system. *Neuron.* 1995, 14:519-26.
Kirkpatrick LL, Matzuk MM, Dodds DC, et al. Biochemical interactions of the neuronal pentraxins. Neuronal pentraxin (NP) receptor binds to taipoxin-associated calcium-binding protein 49 via NP1 and NP2. *J Biol Chem.* 2000, 275:11786-92.
DeGregorio-Rocasolano N, Gasull T, Trullas R. Overexpression of neuronal pentraxin 1 is involved in neuronal death evoked by low K(+) in cerebellar granule cells. *J Biol Chem.* 2001, 276:796-803.
Bootcov MR, Bauskin AR, Valenzuela SM, et al. MIC-1, a novel macrophage inhibitory cytokine, is a divergent member of the TGF-beta superfamily. *Proc Natl Acad Sci U S A.* 1997, 94:11514-9.
Bauskin AR, Zhang HP, Fairlie WD, et al. The propeptide of macrophage inhibitory cytokine (MIC-1), a TGF-beta superfamily member, acts as a quality control determinant for correctly folded MIC-1. *Embo J.* 2000, 19:2212-20.
Lin WJ, Chang YF, Wang WL, et al. Mitogen-stimulated TIS21 protein interacts with a protein-kinase-Calpha-binding protein rPICK1. *Biochem J.* 2001, 354:635-43.
Lin WJ, Gary JD, Yang MC, et al. The mammalian immediate-early TIS21 protein and the leukemia-associated BTG1 protein interact with a protein-arginine N-methyltransferase. *J Biol Chem.* 1996, 271:15034-44.
Prevot D, Morel AP, Voeltzel T, et al. Relationships of the antiproliferative proteins BTG1 and BTG2 with CAF1, the human homolog of a component of the yeast CCR4 transcriptional complex: involvement in estrogen receptor alpha signaling pathway. *J. Biol Chem.* 2001, 276:9640-8.
Rouault JP, Falette N, Guehe nneux F, et al. Identification of BTG2, an antiproliferative p53-dependent component of the DNA damage cellular response pathway. *Nat Genet.* 1996, 14:482-6.
Fong AM, Erickson HP, Zachariah JP, et al. Ultrastructure and function of the fractalkine mucin domain in CX(3)C chemokine domain presentation. *J Biol Chem.* 2000, 275:3781-6.
Imai T, Hieshima K, Haskell C, et al. Identification and molecular characterization of fractalkine receptor CX3CR1, which mediates both leukocyte migration and adhesion. *Cell.* 1997, 91:521-30.
Maciejewski-Lenoir D, Chen S, Feng L, et al. Characterization of fractalkine in rat brain cells: migratory and activation signals for CX3CR-1-expression microglia. *J Immunol.* 1999, 163:1628-35.
Feng L, Chen S, Garcia GE, et al. Prevention of crescentic glomerulonephritis by immunoneutralization of the fractalkine receptor CX3CR1 rapid communication. *Kidney Int.* 1999, 56:612-20.
Zujovic V, Schussler N, Jourdain D, et al. In vivo neutralization of endogenous brain fractalkine increases hippocampal TNFalpha and 8-isoprostane production induced by intracerebroventricular injection of LPS. *J Neuroimmunol.* 2001, 115:135-43.
Ludwig A, Berkhout T, Moores K, et al. Fractalkine is expressed by smooth muscle cells in response to IFN-gamma and TNF-alpha and is modulated by metalloproteinase activity. *J Immunol.* 2002, 168:604-12.
Bradbury A, Possenti R, Shooter EM, et al. Molecular cloning of PC3, a putatively secreted protein whose mRNA is induced by nerve growth factor and depolarization. *Proc Natl Acad Sci USA* 1991. 88:3353-7.
Sigma® Product Information Sheet for Fractalkine, Extracellular Domain (Prod. No. F8676) (Aug. 2001) http://www.sigmaaldrich.com/sigma/datasheet/f867dat.pdf.
A.W. Clowes, et al., "Kinetics of Cellular Proliferation After Arterial Injury. I. Smooth Muscle Growth in the Absence of Endothelium," *Lab Invest.* 49(3): 327-33 (Sep. 1983) Abstract.
A.W. Clowes, et al., "Mechanisms of Steroids After Arterial Injury," *Lab Invest.* 49(2):208-15 (Aug. 1983) Abstract.

(Continued)

*Primary Examiner*—Robert A. Wax
(74) *Attorney, Agent, or Firm*—Conley Rose, P.C.

(57) ABSTRACT

Compositions and methods are disclosed which employ PARIS proteins that are useful for suppressing proliferation of smooth muscle cells. Preferred PARISs are soluble proteins that are secreted by vascular smooth muscle cells, and include PARIS-1 (neuronal pentraxin 1), PARIS-2 (SBP (MIC-1, GDF-15), PARIS-3 (BTG2) and PARIS-4 (soluble fractalkine). Methods of preventing or treating restenosis by administering the new compositions are disclosed. Also disclosed are methods for treating patients undergoing angioplasty procedures, patients with atherosclerosis, and patients with other proliferative disorders, in order to suppress the growth of vascular smooth muscle cells or other cells that play a role in the particular proliferative disorder or condition. A method of screening mRNAs and identifying genes encoding PARISs is also disclosed.

9 Claims, 13 Drawing Sheets

OTHER PUBLICATIONS

M. Nobuyoshi, et al., "Restenosis After Successful Percutaneous Transluminal Coronary Angioplasty: Serial Angiographic Follow-Up of 229 Patients," *J. Am. Coll. Cardiol.* 12(3):616-23 (Sep. 1988) Abstract.

X. Chen, et al., "Restenosis: Emerging Molecular Targets: Going Beyond Drug-Eluting Stents," *Drug Discovery Today*, vol. 2, No. 1: 1-9 (2005).

M. Waldhoer, et al., "Murine Cytomegalovirus (CMV) M33 and Human CMV US28 Receptors Exhibit Similar Constitutive Signaling Activities," *Journal of Virology*, vol. 76, No. 16: 8161-8168 (Aug. 2002).

Chandrasekar, B., "Fractalkine (CX3CL1) stimulated by nuclear factor kB (NF-kB)-dependent inflammatory signals induces aortic smooth muscle cell proliferation through an autocrine pathway," Biochem J. (May 2, 2003) 373, 547-558 (Great Britain).

* cited by examiner

COMPOSITION AND METHOD FOR TREATMENT AND PREVENTION OF RESTENOSIS

STATEMENT REGARDING FEDERALLY SPONSORED RESEARCH OR DEVELOPMENT

This invention was made in whole or in part with funding from the National Heart, Lung, and Blood Institute of the National Institutes of Health (Grant No. HL068024). Accordingly, the United States Government has certain rights in this invention.

CROSS-REFERENCE TO RELATED APPLICATIONS

Not applicable.

BACKGROUND OF THE INVENTION

1. Technical Field of the Invention

The present invention generally relates to compositions and methods for prevention of proliferative disorders, including restenosis, atherosclerosis and cancer. More particularly, the invention relates to compositions containing molecules secreted by cells and which are capable of inhibiting proliferation of those and/or other cells. The invention also relates to therapeutic methods employing such compositions.

2. Description of Related Art

Percutaneous transluminal coronary interventions ("PCI") such as angioplasty procedures are common practice today for relieving atherosclerotic blockage caused by fatty acid deposits in coronary arteries, whereby blood flow is restored in the affected arteries. A relatively common complication of angioplasty is restenosis, a renarrowing of the blood flow due to uncontrolled proliferation of smooth muscle cells at the angioplasty site. Post-angioplasty restenosis was first treated by balloon redilatation and, when stents became available[1], by stent implantation[2]. However, close to 20% of patients developed restenosis within the stent ("in-stent restenosis")[2], due to neointimal VSMC growth[3]. In-stent restenosis was initially treated by repeat angioplasty, rotational atherectomy, laser angioplasty, "stent-in-stent", and other techniques, but all of those procedures yielded suboptimal outcomes[4]. Brachytherapy has been investigated for preventing restenosis[12,13] after primary angioplasty, however, at least 15% of patients treated with brachytherapy still develop restenosis, suggesting that the prevention of restenosis by brachytherapy is not entirely efficacious[13]. It has been reported that brachytherapy only moderately reduced the recurrence rate of in-stent restenosis (from 43.8% to 28.2%)[5], at the expense of adverse radiation exposure both to patients and operators and of late-occurring, intralesional thrombosis.

Among a number of pharmacological interventions attempted, only a few preventive strategies, such as probucol[6], trapidil[7], cilostazol[8], n-3 fatty acid (eicosapentaenoic acid)[9], and folic acid combined with vitamin B12 and pyridoxine[10], have been found acceptable. Even in the better trials, restenosis still developed in 17.9–24.2% of patients. When stent implantation was used to treat primary lesions in order to prevent restenosis, a significant number (18%) of patients who underwent stent implantation experienced restenosis nevertheless[1,2,11]. It has been reported that stents coated with sirolimus (also known as rapamycin) are more effective than conventional stents in a randomized, double-blind clinical trial[55], and recently the FDA has approved a sirolimus-eluting coronary stent for angioplasty procedures to open clogged coronary arteries. Long-term effects and side-effect profiles of sirolimus have not been determined in a large clinical trail, however.

Although brachytherapy and sirolimus-eluting stents may effectively treat a selected group of patients with restenosis, those treatment modalities are likely to remain very expensive and exclusive. For example, the cost of sirolimus-eluting stents is estimated to be four times higher than that of conventional stents, while brachytherapy requires the involvement of radiation oncologists and nuclear physicists. It has been estimated that up to a million PCIs are being performed annually in North America alone[14]. A therapeutically viable, lower-cost treatment that can significantly reduce the risk of restenosis is greatly needed. It has been calculated that a treatment that reduces risk of restenosis by 25–33% risk reduction would save approximately $1,400–$2,000 per patient in hospital, procedural and professional fees, with a total savings in North America alone of $400–800 million a year[15].

SUMMARY OF THE PREFERRED EMBODIMENTS

In the course of investigations leading up to the present invention, it was discovered that certain soluble proteins ("PARISs") normally secreted by vascular smooth muscle cells ("VSMC") are also able to inhibit VSMC growth. Since it is well known in the field of cardiovascular medicine that VSMC cells play a critical role in restenosis and atherosclerosis, it is now proposed that PARISs can be effectively employed to treat, deter or even prevent restenosis and atherosclerosis progression. Some PARISs also appear to be normally secreted by a variety of cells, including non-vascular SMCs. In some cases the PARISs are secreted to a lesser degree than in VSMCs. However, this unique group of proteins hold promise as inhibitors of cell growth in a variety of tissues, and may find use in treating or deterring cell proliferation in a variety of proliferative disorders such as keloid formation, venous grafts, coronary arteries of transplanted hearts and cancers.

Individually, the representative proteins disclosed herein as PARIS-1, PARIS-2, PARIS-3 and PARIS-4, have little or no common homology or mutual family associations. Each has previously been assigned another name and a different implicated function has been attributed to it. While some amino acid sequence information is available for these proteins and some of their physical properties have been described by others, these proteins are not well characterized and their implicated biological functions are different than the bioactivity disclosed herein for the first time (i.e., their inhibitory effects on vascular smooth muscle cell growth and, potentially, other cells.) In accordance with certain embodiments of the present invention, compositions are provided which contain one or more purified PARIS, and may include a suitable carrier (e.g., sterile isotonic saline). For example, the composition may be suitable for direct injection at the desired site of action in a vessel. In certain embodiments the composition is useful for preventing or treating restenosis. In certain preferred embodiments the composition comprises at least one soluble protein secreted from a VSMC and capable of inhibiting VSMC growth, with or without a carrier. For the purposes of this disclosure, the term "soluble protein" has its usual meaning and includes secreted non-matrix proteins. The PARIS may be a natural or synthetic protein, or a biologically active portion thereof.

Certain preferred PARIS proteins from rat have the amino acid sequence identified as GenBank Accession No. P47971 (*R. norvegicus*) (*H. sapiens* ortholog: Q15818) (PARIS-1), GenBank Accession No. Q9Z0J6 (*R. norvegicus*) (*H. sapiens* ortholog: NP_004855) (PARIS-2), GenBank Accession No. A40443 (*R. norvegicus*) (*H. sapiens* ortholog: P78543) (PARIS-3), and GenBank Accession No. O55145 (*R. norvegicus*) (*H. sapiens* ortholog: NP_002987) (PARIS-4). Other PARIS proteins in accordance with certain embodiments of the present invention share at least 40% homology with the above-identified PARISs. 24% amino acid identity with the above-identified rat proteins, preferably sharing at least 40% identity, and still more preferably more than 50% identity.

In another embodiment of the present invention a composition is provided that contains at least two of the proteins: PARIS-1, PARIS-2, PARIS-3 and PARIS-4.

In certain other embodiments of the present invention, methods of using the above-described PARISs and compositions for treatment of patients such as those undergoing angioplasty procedures, patients with atherosclerosis, and patients with other proliferative disorders, in order to suppress the growth of vascular smooth muscle cells or other cells that play a role in the particular proliferative disorder or condition are provided. Advantageously, therapies employing PARISs are potentially less expensive and more inclusive (i.e., they may be administered without special instruments or personnel) than conventional post-angioplasty restenosis treatments and preventatives. Another advantage of employing a PARIS therapeutically is that since PARISs are native proteins, or biologically active portions thereof, no antigen-antibody immune reaction should occur. In some embodiments the proliferative disorder is cancer. In some embodiments the disorder is keloid formation.

In some embodiments a method of deterring or preventing a smooth muscle cell ("SMC") proliferative disorder is provided which includes administering to a site at risk of overgrowth by SMCs a cell growth inhibitory amount of a composition described above. In certain embodiments a method of inhibiting VSMC growth is provided which comprises administering to a VSMC at least one PARIS protein, preferably PARIS-1, PARIS-2, PARIS-3 or PARIS-4.

In some embodiments a method of preventing post-angioplasty restenosis is provided which includes administering to an above-described protein or composition to an angioplasty site.

In some embodiments a method of deterring or preventing atherosclerosis progression is provided which includes administering to a site at risk of overgrowth by vascular smooth muscle cells a cell growth inhibitory amount of a protein or composition as described above. The PARISs may be administered via a PARIS-eluting stent or other local drug delivery system, or they may be administered systemically, percutaneously, sublingually, or rectally.

In still other embodiments of the present invention, a screening method for detecting an inhibitor of SMC proliferation is provided. The method comprises:

a) extracting RNAs from the growing vascular smooth muscle cells from a first animal model that is restenosis-resistant with respect to balloon injury to a blood vessel in the first animal model (e.g., Harlan SD rat), followed by the generation of the pool of which are labeled with a suitable fluorescent marker.

b) extracting RNAs from the growing vascular smooth muscle cells from a second animal model (e.g., Sasco SD rat) that is restenosis-prone with respect to balloon injury of a blood vessel in the second animal model, followed by the generation of the pool of cDNAs, which are labeled with a suitable fluorescent marker.

c) performing microarray analyses to identify genes that are abundantly present in the first set of cDNA pool but scarcely present in the second set of cDNA pool, followed by identification of genes that encode soluble proteins that are secreted by the vascular smooth muscle cells from the first animal model more abundantly than from the second animal model. Alternatively, another molecular biological technique could be substituted, such as subtraction cloning, to identify genes that are differentially present between the first and the second animal models.

d) assaying the protein levels to validate that proteins encoded by these genes are in fact upregulated in the vascular smooth muscle cells from the first, but not as much as in the second, animal model.

e) expressing and purifying these proteins and confirming that these proteins, in fact, suppress the growth of vascular smooth muscle cells.

The method may also include identifying homologs or biologically active portions of the/those protein(s). In certain embodiments the expression level of the upregulated gene is greater in growing cells from the first animal model than in those from the second animal model, preferably at least 1.5-fold, and more preferably at least 3-fold greater. These and other embodiments, features and advantages of the present invention will become apparent with reference to the following description and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A: Intimal area in control and balloon injured Harlan and Sasco rats; FIG. 3B: Ratio of intimal to medial area for control and injured Harlan and Sasco rats; FIG. 3C: Medial area in control and balloon injured Harlan and Sasco rats.

FIG. 4A: Harlan and Sasco cells in sub-confluent and confluent cultures. FIG. 4B: α-actin and DAPI staining showing differentiation of Harlan and Sasco and VSMCs, and U2OS cells as negative control.

FIG. 15A: media after 24 hrs incubation. FIG. 15B: media after 48 hrs incubation. FIG. 15C: PARIS-4 secretion rate ($hr^{-1}$).

FIG. 18A illustrates the TSA-enhanced immunohistochemistry method. FIG. 18B Photograph (×100) TSA-stained restenotic tissue (Sasco SD rat) (Left panel) no anti-PARIS-4 antibody. (Right panel) Anti-PARIS-4 antibody present. M denotes media. FIG. 18C is a comparison of PARIS-4 expression in Harlan and Sasco restenotic tissues (×40). (Left panel) Sasco balloon-injured carotid arteries. (Right panel) Harlan balloon-injured carotid arteries. * denotes clot formation within the lumen of the artery. Open arrows indicate the absence of PARIS-4 signal in Sasco neointima (left panel); closed arrows indicate the strong PARIS-4 signals seen in Harlan neointima (right panel). FIG. 18D shows DAB signal intensities expressed in an arbitrary unit. (Right panel) DAB signal of Harlan neointima. (Left panel) DAB signal of Sasco neointima.

FIG. 19A depicts schematically a procedure for producing a recombinant DNA construct AcMNPV-PARIS-4 and -LUC, containing PARIS-4 and Luciferase, respectively. FIG. 19B the results of a Western blot analysis of the proteins produced by the recombinant DNA of FIG. 19A. FIG. 19C is a photograph of a Coomassie Blue stained gel electrophoresis of the Ni-NTA purified proteins from the constructs of FIG. 19B.

DETAILED DESCRIPTION OF THE PREFERRED EMBODIMENTS

Research efforts on post-angioplasty restenosis and atherosclerosis have conventionally focused primarily on the molecules that cause smooth muscle cells to grow. Little attention has been paid previously to molecules that prevent cells from growing (i.e., inhibitors or negative regulators of cell proliferation). It is believed that no molecules have been previously reported that are secreted from vascular smooth muscle cells and which inhibit vascular smooth muscle cell growth. The four proteins (PARIS 1–4) described herein are believed to be the first such inhibitors that are capable of inhibiting smooth muscle cell growth in vitro and in vivo.

Restenosis-Resistant and Restenosis-Prone Animal Models

Figure 1:
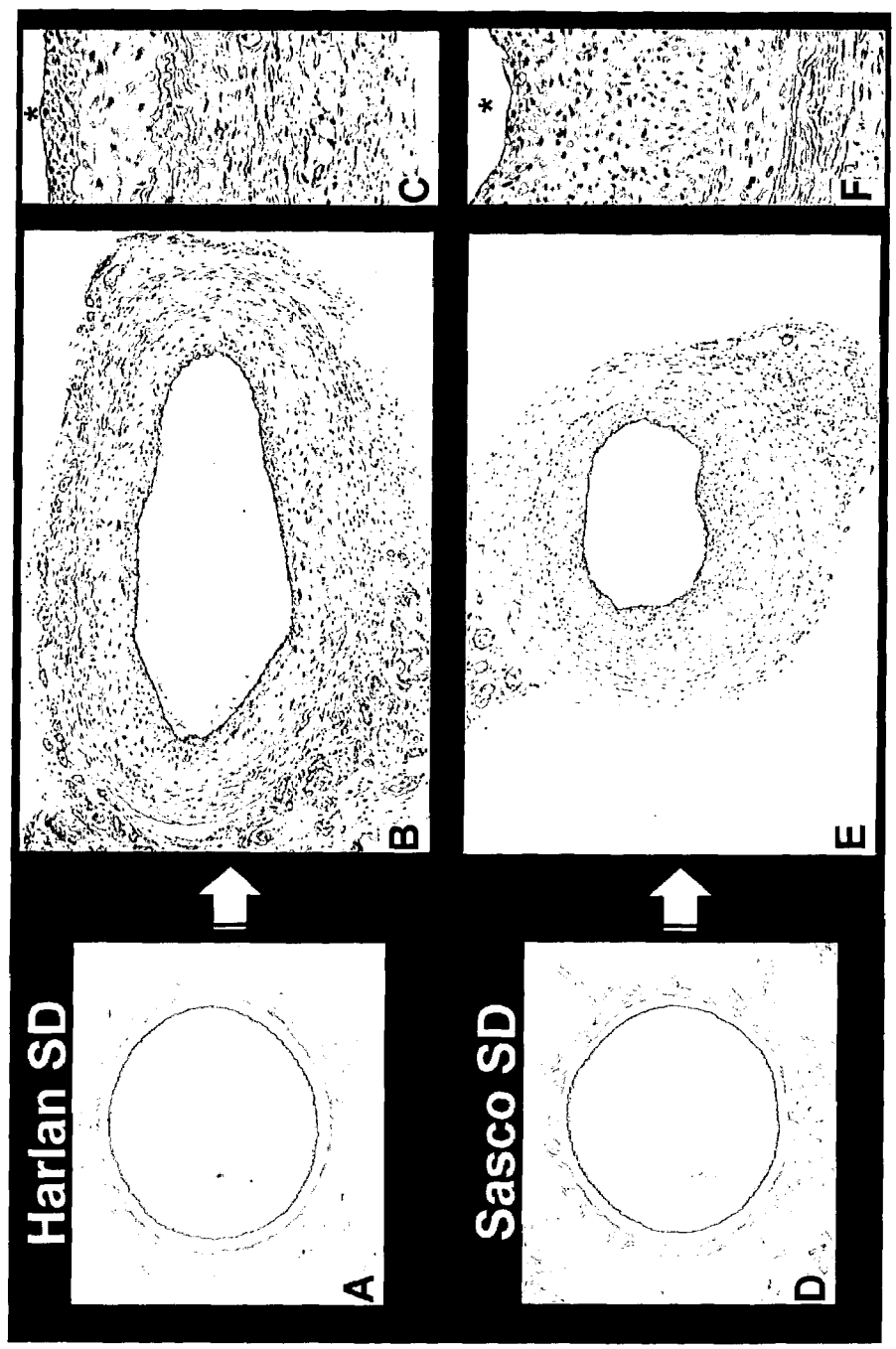
FIG. 1 is a group of photographs showing the status of neointimal formation in Harlan and Sasco SD rat carotid arteries 14 days after balloon injury. Panels A and D: Pre-angioplasty; Panels B, C, E and F: Post-angioplasty. Panels A and B: Harlan X50; Panel C: Harlan X200; Panels D and E: Sasco X50; Panel F: Sasco x200. The asterisk (*) denotes the vessel lumen.

Rat substrains with restenosis-resistant and restenosis-prone phenotypes were employed an animal models in the present investigations. It had been observed in a number of animal surgeries at the University of Texas Health Science Center at Houston that more robust neointima sometimes appeared to form in the carotid arteries of one substrain of rat than in those of another substrain after the same balloon angioplasty procedures were performed. In order to investigate that possibility, substrains of Sprague-Dawley rat were obtained from two different vendors (i.e., Harlan and Sasco). The degree of neointimal proliferation in 12 rats from each group was determined using a standard carotid artery balloon injury-restenosis model, as described by Clowes et al.[16] Three rats from each group (a total of 6 rats) were sacrificed on days 1, 3, 7 and 14 after the surgical intervention. Right and left carotid arteries were harvested, fixed in 4% neutral buffered formalin, and then embedded in paraffin. Sectioned tissues were stained with hematoxylin-eosin (HE) and subjected to morphometric analysis and cell counting. In FIG. 1, groups of photomicrographs showing the status of neointimal formation in Harlan and Sasco rat carotid arteries 14 days after balloon injury are as follows: Panels A and B: Harlan X50; Panel C: Harlan X200; Panels D and E: Sasco X50; Panel F: Sasco X200. Panels A and D: Pre-angioplasty; Panels B, C, E and F: Post-angioplasty. In Panels C and F, the asterisk (*) denotes the vessel lumen.

The experimental protocol was as follows: Male Sprague-Dawley (SD) rats (400–450 gram) were purchased from the Sasco branch of Charles River Laboratories ("Sasco", Kingston, N.Y.) and from Harlan Inc. ("Harlan", Indianapolis, Ind.). All the animals were housed individually and cared for in accordance with institutional animal welfare guidelines. Rats were allowed standard rat chow and water ad labium and were on 12 hour-light-dark cycles. In brief, individual rats (total number: 24) were weighed, then anesthetized with halothane (Halocarbon Laboratories, River Edge, N.J.), using a vaporizer (Vapomatic Sterline, Mass.). Surgical areas on the inside left hind limb and the ventral neck region were shaved, cleaned with providine, and a sterile drape placed over the animal with opening at the surgical sites. A midline neck incision was made to expose the left common carotid artery; the iliac artery was exposed through another incision above its junction with the femoral artery, then ligated at the distal end. The right common carotid artery served as a control. A 2F Fogarty arterial embolectomy catheter (Baxter Healthcare Corporation, Santa Ana, Calif.) was inserted into the iliac artery and passed through the aorta to the distal portion of the left common carotid artery. Placement of the catheter was checked via midline incision in the neck. The balloon catheter was inflated with a manually driven inflator device (Encore, Scimed, Maple, Minn.) to 2.5 atmospheres, then retracted in the inflated position to the origin of the left common carotid artery at the aorta. The catheter was deflated, returned to its original position, inflated, and retracted through the carotid artery twice again. The Forgarty catheter was removed via the iliac artery, which was loigated proximal to the incision site; skin was closed in both the neck and hind limb, and the incision sites were treated with topical antibiotics. Six rats (3 each from Harlan and Sasco) were killed on the 1, 3, 7 and 14 days after the surgical intervention. Rats were euthanized with carbon dioxide gas inhalation, the abdomen opened, and a catheter inserted through the aorta to the arch. The 20 mL of heparinized PBS was infused at 5 mL/min, at which time, the right and left carotid arteries were dissected out. The middle one third of each carotid artery was harvested and placed in 4% neutral buffered formalin solution (Fisher Scientific, Pittsburgh, Pa.). Paraffin embedded tissues were sectioned at 4 μm thickness and Hematoxylin-Eosin (HE) staining was performed on each tissue. As is shown in FIG. 1, Harlan and Sasco SD rats had obvious, strikingly different patterns of response to the balloon injury. The neointima of Harlan SD rats was uniformly thinner than that of Sasco SD rats.

Figure 2:
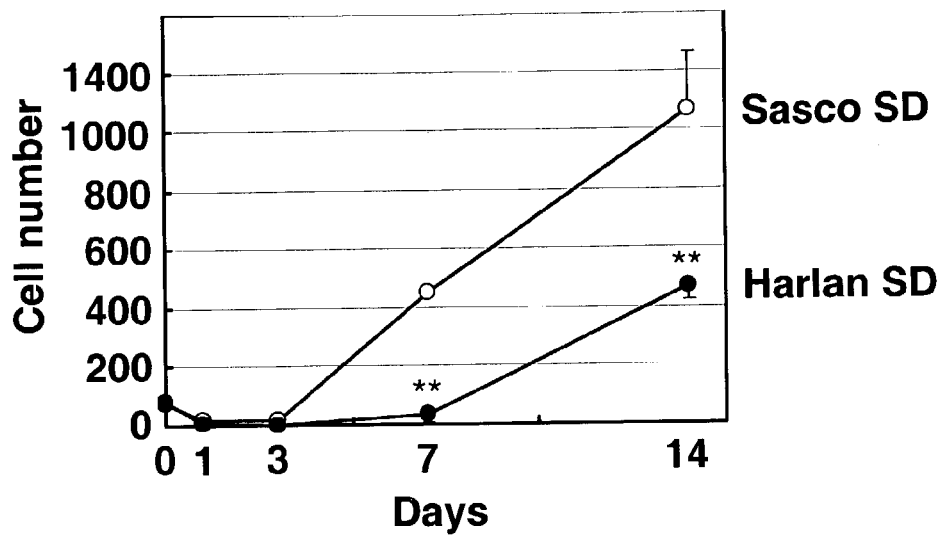
FIG. 2 is a graph showing cell growth/neointima development over a 14 day period following balloon injury in Sasco SD rats.

Referring now to FIG. 2, Sasco SD rats developed neointima in response to balloon injury far more aggressively than did Harlan SD rats. Hematoxin-eosin stained sections of rat carotid arteries (balloon-injured) were subjected to the determination of the number of the nuclei in the neointima. 0: Uninjured rat carotid arteries. The double asterisks (**) denotes $P<0.01$ by Student's two sample T-test. Although there were no differences in neointimal cell numbers between Sasco and Harlan SD rats in 0, 1, and 3 days after the injury, a striking difference in the number of the nuclei in the neointima was obvious on $7^{th}$ and $14^{th}$ days after the injury. At $14^{th}$ day, Sasco had 1064.8±195 cells in the neointima while Harlan had only 469±46.4 cells, $P<0.01$)

The counting of HE-positive nuclei in the intima revealed that the intima of Sasco SD rats contained significantly more cells on $7^{th}$ and $14^{th}$ days than did that of Harlan SD rats (FIG. 2).

Figure 3A:
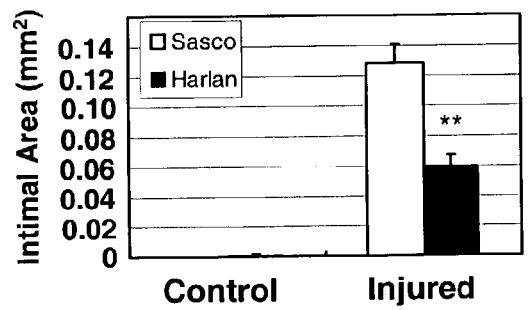
FIGS. 3A–C are graphs showing the results of morphometric analysis of Harlan and Sasco SD rat carotid arteries 14 days after balloon injury.
Figure 3B:
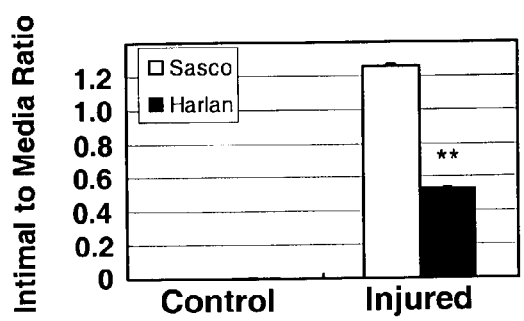
Figure 3C:
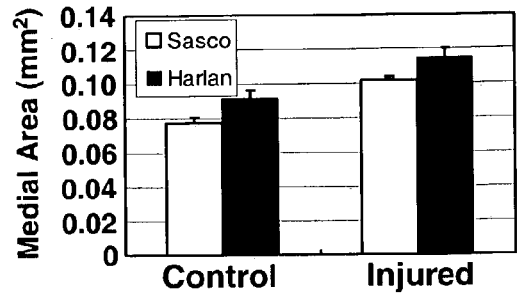

FIGS. 3A–C show the results of morphometric analysis of Harlan and Sasco carotid arteries 14 days after balloon injury showed the restenosis-resistant phenotype in Harlan SD rats. The HE stained section of rat carotid arteries were analyzed by the BIOMAX-BX40 triocular microscope (Olympus, Tokyo, Japan) connected to CCD-IRIS video camera (Sony, Tokyo, Japan) which allowed the projection of the entire observed field on the screen of a TV monitor. The areas [mm2] of the intima and media were measured with the aid of the JAVA computerized image analysis system (Jandel Scientific, Corte Madera, Calif.). FIG. 3A: Intimal areas were significantly larger in Sasco than in Harlan (N=6) FIG. 3B: Intima to media ratio was calculated as (Intimal area)/(Medial area). FIG. 3C: The media of Harlan was slightly (not significantly) larger both before and after the balloon injury. The double asterisk (**) denotes $P<0.01$ by Student's two sample T-test. A morphometric analysis showed both the intima-to-media ratio (IMR) and intimal area to be significantly larger in Sasco SD rats than in Harlan SD rats (FIG. 3). These data suggested that the carotid arteries of Harlan and Sasco SD rats responded quite differently to the same vascular injury and that Sasco SD rats had significantly more neointimal formation than did Harlan SD rats (FIGS. 1–3).

The Harlan and Sasco SD animal lines were investigated as to their lineage. Harlan and Sasco SD rats have the same ancestors, rats from Sprague-Dawley Co. established by Dr. Dawley in the mid 1970's. Harlan Co. and Sasco Co. (later purchased by Charles River Laboratories) initiated their own breeding programs in 1981 and 1979, respectively. The breeding protocols of their companies have not changed since colonies were first established (Communication with scientists of Harlan Co. and Charles River Laboratories). Despite sharing the same ancestors, Harlan and Sasco SD rats exhibit clearly different phenotypes, as summarized in Table 1. Notably, Sasco SD rats are significantly heavier than Harlan SD rats later in life, despite the comparable food consumption[17,18]. Sasco SD rats also exhibit different behavioral[19], neuroanatomical[20,21], endocrinological[21], immunological[22], and cardiovascular[22] phenotypes (Table 1). These observations suggest that Harlan and Sasco SD rats represent two genetically divergent substrains derived from the same ancestors.

TABLE 1

HARLAN AND SASCO SPRAGUE-DAWLEY RATS.

| | | | Harlan SD | Sasco SD |
|---|---|---|---|---|
| Substrains | | | Harlan SD | Sasco SD |
| Vendor | | | Harlan Co. | Charles River Laboratories |
| Breeding Facilities | | | Houston, TX and other locations | Kingston, NY |
| History | | | Colony originally established in 1981 when Harlan purchased Sprague-Dawley company established by Dr. Dawley (His wife's maiden name was Sprague). Five breeding facilities established under the same breeding protocol since 1981. | Colony originally established in Madison WI in 1979 by Sasco Co., which apparently purchased the breeding pairs from Sprague-Dawley company. Sasco Co. was subsequently purchased by Charles River in 1992; Moved to Omaha, NE in 1994, Moved to Kingston, NY in 1996. The same breeding protocol has been used since 1979. |
| General Clinical comparison | In-life palpable mass | | Male (41%), Female (89%)[56] | Male (42%), Female (84%) |
| | Chronic renal disease | | Male (78%), Female (10%) | Male (38%), Female (11%) |
| | Pituitary mass | | Male (8%), Female (48%) | Male (48%), Female (86%) |
| | 105 week survival | | Male (15%), Female (45%) | Male (20%), Female (25%) |
| | Weight at termination | | Male (528 g), Female (329 g)[56,57] | Male (788 g), Female (562 g) |
| | Food consumption | | Male (0.13 kcal/day/weight), Female (0.217) | Male (0.115), Female (0.109) |

TABLE 1-continued

HARLAN AND SASCO SPRAGUE-DAWLEY RATS.

| | | | |
|---|---|---|---|
| Neurological function | Long-term facilitation (LTF) | Less pronounced[58] | More pronounced |
| | Spinal projection of neurons | Locus coeruleus projected more to dorsal horn; Nucleus subcoeruleus projected more to dorsal horn[59] | Locus coeruleus projected more to ventral horn; Nucleus subcoeruleus projected more to ventral horn |
| | Locus coeruleus derived antinociception | α-2 adrenoceptor mediated[60] | Not α-2 adrenoceptor mediated |
| Inflammatory reaction | ACTH production in response to LPS | Smaller[61] | Larger |
| | IL-6 production in response to IL-1β | Larger[61] | Smaller |
| Cardiovascular | Hypertensive response with NOS inhibition | Higher BP[61] | Lower BP |

Legend:
SD: Sprague-Dawley;
LTF: a prolonged, serotonin-dependent augmentation of respiratory motor output following episodic hypoxia;
ACTH: adrenocorticotropin;
LPS: lipopolysaccharide;
NOS, nitric oxide synthase.

As described above and shown in FIGS. 1–3, Harlan and Sasco rat carotid arteries respond to vascular injury in very different ways. Since these substrains exhibit various phenotypic differences (Table 1), the phenotypic difference in the response of the artery to the injury may be due to the genetic difference in endothelial cells, VSMCs, platelets, leukocytes, or any other cells that play a role in restenosis. Given the fact that a number of published studies strongly suggest the critical role of VSMCs in restenosis, it was hypothesized that the phenotypic difference in the response of rat carotid arteries to injury is, at least partially caused by the genetic differences in Harlan and Sasco VSMCs. In order to test that hypothesis, the following series of experiments were carried out on VSMCs isolated from the normal carotid arteries of Harlan and Sasco SD rats.

EXAMPLE 1

VSMCs from Harlan SD Rats Grow More Slowly

Figure 4A:
FIGS. 4A–B are photomicrographs showing that Harlan and Sasco SD rat vascular smooth muscle cells do not differ morphologically.
Figure 4A:
Figure 4A:
Figure 4A:
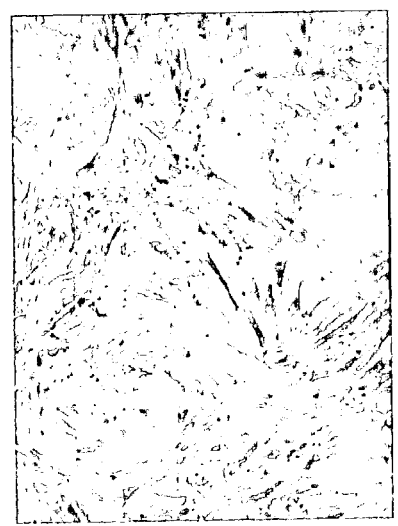
Figure 4B:
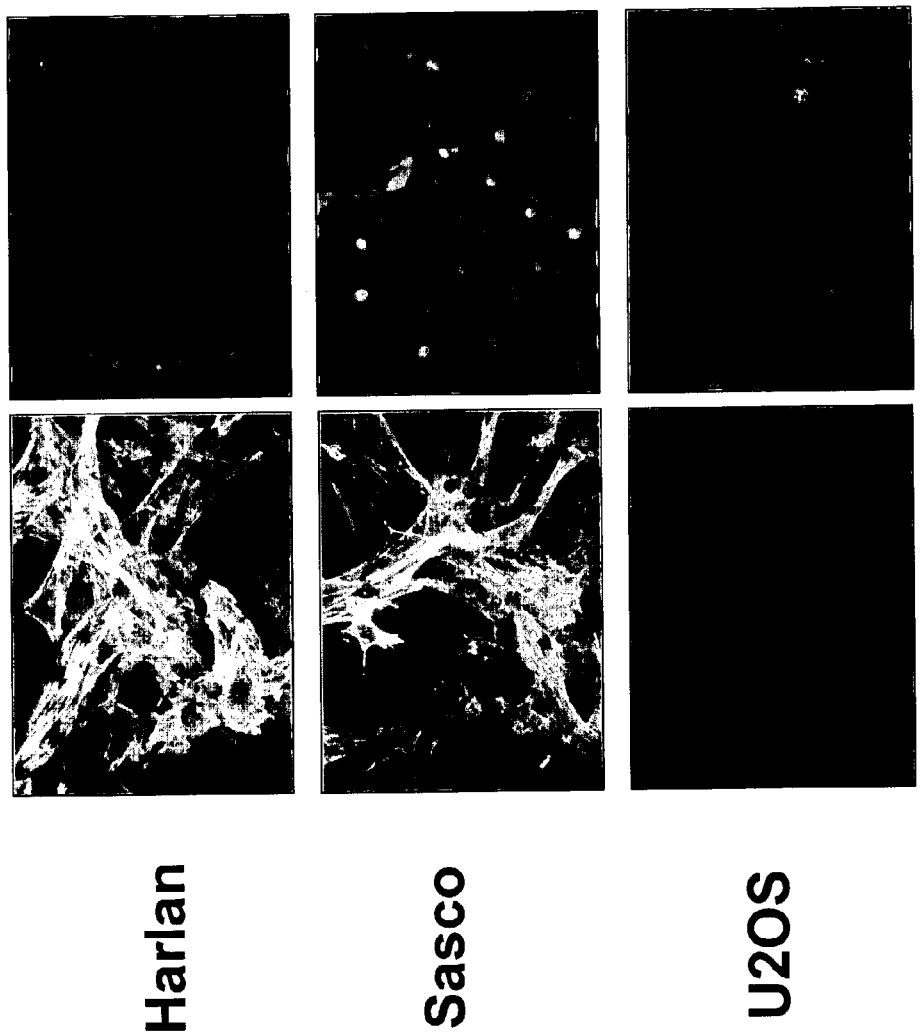

Equal numbers of Harlan and Sasco SD rat VSMCs were seeded in 6-well plates, synchronized, and subjected to the same growth media. As shown in FIGS. 4A–B, Harlan and Sasco VSMCs do not differ morphologically. In order to test whether a drastic phenotypic difference observed in Harlan and Sasco SD rats in response to balloon injury was due to, at least partially, the genetic difference of two rat VSMCs to growth stimuli, Harlan and Sasco VSMCs were first isolated from carotid arteries of these animals. FIG. 4A: Under microscopy, both VSMCs looked identical under subconfluent and confluent conditions. FIG. 4B: Differentiation assay showed that both Harlan and Sasco differentiated in Differentiation Media (0.5% serum; 50 μg/mL heparin) equally showing α-actin in>90% of cells in 7 days. For comparative purposes, the U2OS cancer cell line from human osteosarcoma was cultured under similar conditions and did not differentiate.

Figure 5:
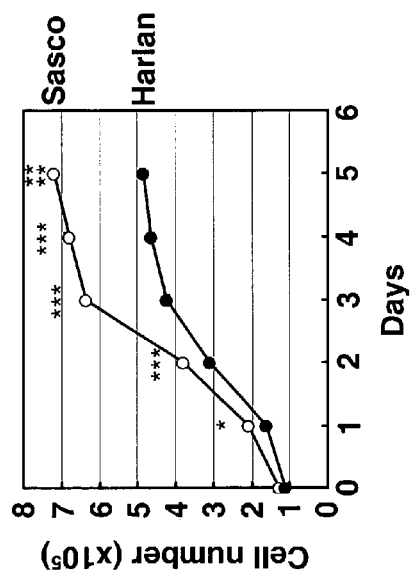
FIG. 5 is a graph comparing cell growth of Sasco and Harlan SD rat VSMCs in tissue culture over a 6 day period under the same cell culture conditions.

Although the VSMCs from the two substrains did not differ morphologically (FIGS. 4A–B) and were placed in the exact same microenvironment, VSMCs from Harlan SD rats grew much more slowly than did those from Sasco SD rats (FIG. 5). In order to determine the growth rate of Harlan and Sasco VSMCs under the same environment, $1 \times 10^5$ cells (the passage 5) were seeded in duplicate in 6-well dishes, synchronized by serum starvation, and stimulated with serum on Day 0. The number of cells in each well was determined every 24 hours for 6 days. *: P<0.05, *: P<0.005, **: P<0.001 by Student's two sample T-test. A graph showing the results of the growth assay reveals the slower growth of Harlan VSMCs in comparison with Sasco VSMCs.

EXAMPLE 2

VSMCs from Harlan SD Rats Take Up Much Less Thymidine

Figure 6:
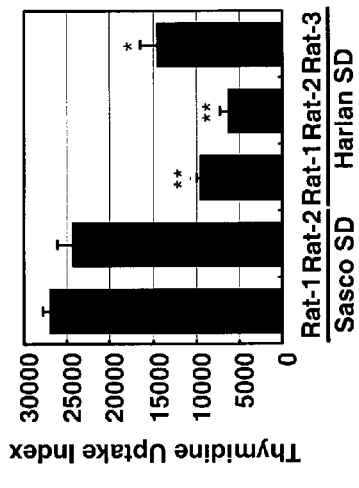
FIG. 6 is a bar graph showing thymidine incorporation by Sasco SD VSMCs and Harlan DS VSMCs under the same cell culture conditions.

In order to test the hypothesis that the observed difference in the growth rates of Harlan and Sasco VSMCs was due to a difference in the rate of DNA synthesis, a standard thymidine incorporation assay was performed. Referring to FIG. 6, the thymidine incorporation assay shows the larger uptake of thymidine by Sasco SD VSMCs than by Harlan SD VSMCs upon serum stimulation. A standard thymidine incorporation assay was performed using VSMCs from two Sasco SD and three Harlan SD rats of the same (6) passage. After synchronization by serum-starvation, cells were stimulated with 5% serum with 1 μCi/mL of methyl-$H^3$-thymidine for 24 hours. Counts were normalized to protein concentrations. *: P<0.05; **: P<0.01. These data suggest that Harlan VSMCs synthesize DNA more slowly than do Sasco VSMCs.

EXAMPLE 3

VSMCs from Harlan SD Rats are More Susceptible to Noxious Stimuli

Figure 7:
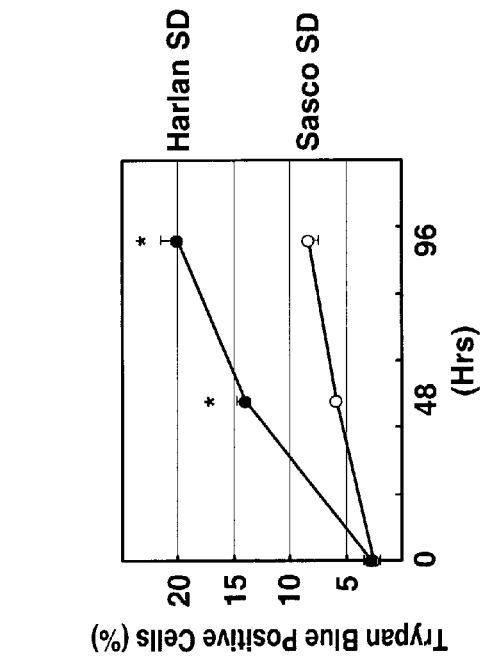
FIG. 7 is a graph showing trypan blue uptake in TNF-α stimulated Harlan and Sasco SD VSMCs in culture.

In order to test the hypothesis that the difference in growth between Harlan and Sasco VSMCs was not only due to a difference in DNA synthesis rate, but also due to a difference in susceptibility to cytotoxicity, we performed a cell death assay in which Harlan and Sasco SD rat VSMCs were challenged with tumor necrosis factor-α (TNF-α) and the number of dead cells were assessed by a trypan-blue exclusion assay. As is shown in FIG. 7, Harlan VSMCs were significantly more susceptible to TNF-α challenge than were Sasco VSMCs. Harlan and Sasco VSMCs were seeded in duplicate at $2 \times 10^5$/well in 6-well dishes. Cells were stimulated by 10 nM TNF-α in M231 media with 0.5% serum supplements for indicated periods of time. Cells were harvested by trypsinization, washed, and pelleted into trypan blue solution and counted under hemocytometer. At least 200 cells were counted. Trypan blue positive cells could not transport out trypan blue dye and were dead. The asterisk (*) denotes a statistical difference of P<0.05 by Student's two sample T-test. It was concluded that Harlan SD cells are more susceptible to TNF-α-induced cell death than Sasco SD cells.

EXAMPLE 4

VSMCs from Harlan Rats Secrete a Soluble Substance that Retards Growth of VSMCs

In order to test the hypothesis that soluble factors from VSMCs influence the growth patterns of Harlan and Sasco VSMCs, the same growth assay was performed with conditioned media from either Harlan or Sasco VSMC cultures. Harlan conditioned media suppressed the growth of Sasco VSMCs and A7r5 VSMCs in contrast to Sasco conditioned media. Double asterisks denote P<0.001 by ANOVA (General linear model) between cells treated with Sasco conditioned media and cells treated with Harlan conditioned media.

The experimental protocol was as follows: $1 \times 10^4$ cells (either Sasco VSMCs or A7r5 VSMCs, which is rat vascular smooth muscle cell line [ATCC, Manassas, Va.]) were seeded on 6-well plates in duplicate. Next day, media were exchanged for Harlan or Sasco conditioned media, which were obtained by exposing 2.0 million Harlan/Sasco VSMCs to fresh Media 231 for 24 hours. The number of cells in each well was determined every 24 hours for 6 days. Strikingly, when VSMCs were incubated with the Harlan conditioned media, their growth rate was slower than that of VSMCs incubated with the Sasco conditioned media (FIG. 8A). This experiment was repeated thrice with the same results. These data suggest that there are soluble factors secreted from Harlan and Sasco VSMCs negatively and positively regulating VSMC growth, respectively, and that these secreted factors explain, at least partially, the sluggish growth of Harlan VSMCs in comparison with that of Sasco VSMCs. The same experiment was performed using the rat smooth muscle cell line A7r5, and the same results were obtained.

As described above and in FIGS. 1–3, it was shown that Sasco SD rat carotid arteries produced much more neointima in response to balloon-injury than did Harlan SD rat carotid arteries. It is of interest to note that in related studies it was also determined that media and adventitia layers do not differ between the Harlan and Sasco animal models after balloon injury (data not shown). It was suggested that the genetic differences between Harlan and Sasco SD rat VSMCs may explain the restenosis-resistant phenotype of Harlan SD rats. When VSMCs were isolated from Sasco and Harlan SD rat carotid arteries and studied, it was shown that the behavior of these two groups of VSMCs in vitro was entirely concordant with that of carotid arteries in vivo (FIGS. 4–7). These data suggested that the difference in neointimal proliferation in Harlan and Sasco SD rats could be at least partly explained by genetic differences of Harlan and Sasco VSMC response to growth stimuli. Furthermore, it was possible that Harlan VSMCs grew more slowly than did Sasco VSMCs because Harlan and Sasco VSMCs secreted negative and positive growth regulatory molecule(s) into the extracellular environment, respectively. At that time, the transcripts of Harlan VSMCs were compared with those of Sasco VSMCs, which were exposed to growth stimuli, using microarray assay system. This study sought to identify the secreted negative growth regulatory molecule(s), if any, by evaluating genes upregulated in Harlan VSMCs.

EXAMPLE 5

Microarray Analysis of Transcripts from Harlan and Sasco SD Rats

Figure 8:
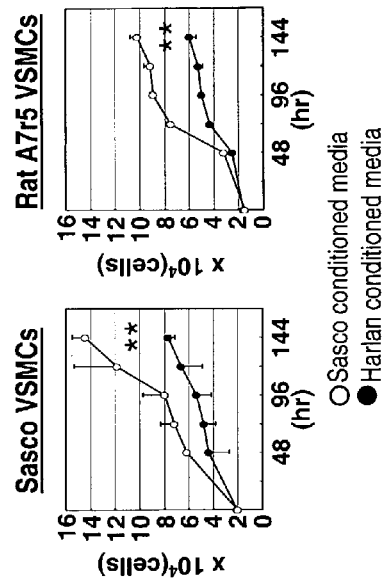
FIG. 8 is a pair of graphs showing growth of Sasco VSMCs or rat A7r5 VSMCs over a 144 hr period in either Harlan or Sasco conditioned media. (Left panel) Sasco VSMCs; (Right panel) Rat A7r5 VSMCs.
Figure 9:
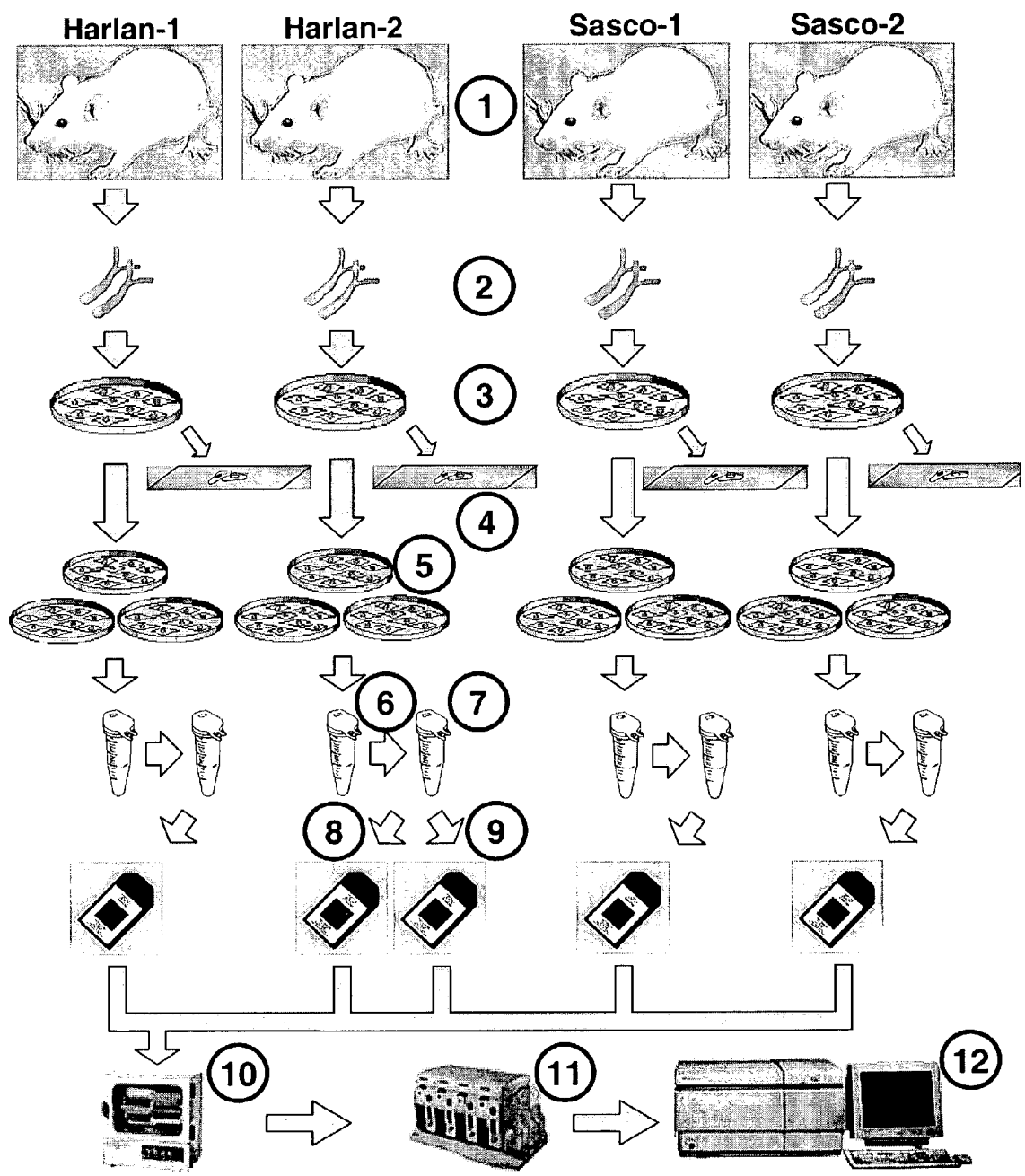
FIG. 9 is a schematic illustration showing the steps of a gene microarray experiment to identify the highly expressed genes in growing Harlan and Sasco SD rat VSMCs.

In order to evaluate the hypothesis that the significant difference in growth pattern of VSMCs observed in vitro and in vivo between Harlan and Sasco SDs (FIGS. 1–8) was due to the difference in the degree and/or presence of the expression of growth-controlling genes, the status of transcripts in growing VSMCs from Harlan SD were compared to that of Sasco SD rats using Affymetrix Rat Arrays (RGU344), as illustrated in FIG. 9. Extreme care was taken to keep the growth condition of both groups identical. The purity of the smooth muscle cell preparation was always confirmed by α-actin staining and was shown to be always higher than 90%.

The experimental protocol of the Affymetrix rat gene array analysis to identify the restenosis related genes was as follows:

Harlan and Sasco SD rats were purchased from Harlan Co. and Charles River Laboratories, respectively, and housed individually and cared for in an identical fashion, according to the institutional guidelines on standard rat chow (Ralston Purina, Richmond, Ind.) and water ad labium with 12 hour light-dark cycles.

(2) Right and left carotid arteries were then harvested. Adventitial layers were carefully removed by brunt dissection under dissecting microscope. The endothelial layers were removed by rubbing a cotton-tipped swab against the endothelial surface of opened arteries several times.

(3) VSMCs were allowed to grow in a 10-cm dish on M231 Media with serum supplements (Cascade Laboratories, Portland, Oreg.).

(4) When cells were confluent, they were propagated into one chamber slide and three 10-cm dishes. Cells in the chamber slide were allowed to differentiate on the Differentiation media (0.5% serum, 50 µg/mL Heparin) for 7 days and stained with anti-α-actin antibody. The purity of VSMCs over 90% was confirmed.

(5) When VSMCs on 10-cm dishes were 80% confluent, cells were harvested.

(6) The total RNA were extracted using a RNeasy™ Midi kit (Qiagen).

(7) The double-stranded complementary DNA (cDNA) was then synthesized, using SuperScript Choice™ system (Gibco BRL), followed by phenol-chloroform extraction and ethanol precipitation. Synthesis of biotin-labeled cRNA was performed using Enzo BioArray High Yield RNA Transcript Labeling Kit™ (Affymetrix), followed by the fragmentation of the cRNA.

(8)–(9) The cRNAs were then subjected to target hybridization. One array (GeneChip®; Rat Genome U34 Set, Affymetrix) per rat was used normally, except for one Harlan rat for which two arrays were used to test reproducibility of the hybridization Hybridization was performed at 45° C. in an Affymetrix Hybridization Oven 640 for 16 hours.

Post-hybridization wash, stain, and post-stain wash were performed in Fluidics Station 400 in a standard fashion.

Finally, arrays were scanned by Affymetrix Scanner System. Then data analysis was performed using d-chip software, as described previously[23]. Replicate data for the same sample was weighted gene-wise using inverse squared standard error as weight[23]. An unpaired two-group comparison for each probe set was performed. This analysis considered both measurement error (as measured by the replicate data) and variation among samples. Genes were determined to have altered gene expression levels if they had a 2-fold or greater change in the means of the 2 groups (the "first" approach, described below) and if a gene was determined to be present in either both groups or in one of the groups (the "second" approach described below).

Figure 10:
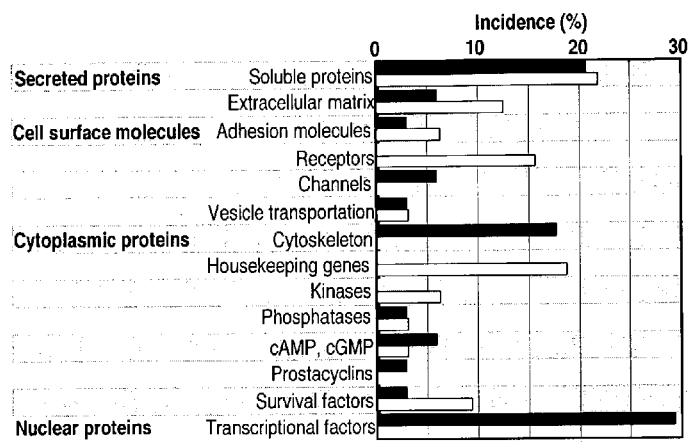
FIG. 10 is a bar graph showing the relative incidence of various groups of genes identified in accordance with the experiment of FIG. 9. Closed bars: Harlan SD VSMCS. Open bars: Sasco SD VSMCs.

A profound difference in gene expression between Harlan and Sasco SD VSMCs was observed. In FIG. 10, the closed bars denote Harlan; open bars denote Sasco. The data acquired by the experiment described in FIG. 9 was analyzed as follows. A Rat Genome U34 GeneChip® contains approximately 7000 full-length sequences and 1000 EST clusters, allowing validation of the array data with the previous works on restenosis and to identify novel genes that may play an important role in restenosis. At least 6 independent array experiments were performed in this study, the results of which are essentially identical.

First, signal intensities of certain genes were compared between Harlan and Sasco and identified genes/ESTs that had more than 3-fold increase (either in Harlan or in Sasco). Data with high standard deviations were excluded from analysis.

Second, the signals that were only present in Harlan and the signals that were only present in Sasco were examined. Genes that were identified by two different algorithms, genes that had multiple "hits" within a single algorithm, and genes that were upregulated (either in Harlan or Sasco)>10 folds were considered to be important genes in the process of restenosis.

Third, these genes were categorized by the intracellular locations and functions and tabulated (Tables 2 and 3). For ESTs without homology to rat genes, Blast search using human and mouse database was performed to identify a human/mouse homolog of the particular EST.

Fourth, for each gene identified to be important, a MedLine search was performed to determine (a) whether these genes have been implicated in restenosis or negative growth regulation, (b) how much characterization was made, and (c) if a particular gene would be a candidate gene in our hypothesis, i.e., secreted soluble non-matrix proteins that may play a role in the negative regulation of VSMC growth. There were striking differences in genes between Harlan and Sasco SD VSMCs. Secreted proteins in Sasco were predominantly growth-promoting while those in Harlan, although poorly characterized, were predominantly negative regulators of cell growth and proliferation. Sasco VSMCs had a number of extracellular matrix (ECM) genes upregulated, along with genes for adhesion molecules, receptors, housekeeping genes, kinases and survival factors. Harlan VSMCs had a number of genes upregulated for transcriptional factors (almost always negative regulator of growths), cytoskeleton and channels. Many genes identified as being associated with restenosis have already been implicated in restenosis by other investigators.

Genes that exhibited a more than 3-fold increase in signal intensity in Harlan and Sasco SD rat VSMCs are presented in simplified fashion in Tables 2 and 3, respectively. Categories of genes overexpressed in Harlan and Sasco SD VSMCs are displayed in bar graph form in FIG. 10.

There was a marked difference in the levels of several transcripts in these animals. The microarray data show a striking difference in gene expression between Harlan and Sasco SD VSMCs. There were 34 and 32 genes whose expression levels were upregulated more than 3-fold in Harlan and Sasco SD rats, respectively. The genes upregulated in the Harlan SD rats were drastically different both categorically and functionally from those in the Sasco SD rats. While Sasco VSMCs upregulated a number of genes for ECM proteins, cell surface receptors (most of them associated with growth and proliferation), house-keeping genes, kinases, and survival factors, Harlan VSMCs upregulated only a small number of these genes. On the contrary, Harlan VSMCs upregulated many genes for transcriptional factors (most of them were associated with growth arrest and apoptosis) and cytoskeletal proteins, which were barely present in Sasco VSMCs. These data suggest that Harlan and Sasco VSMCs, when placed in the exact same growth environment, express drastically different sets of genes. The discoveries that Sasco VSMCs upregulated receptors for growth-promoting molecules, housekeeping genes and survival-related genes and that Harlan VSMCs upregulated transcriptional factors for negative growth regulation and cytoskeleton proteins are intriguingly consistent with the in vivo finding that neointimal formation was far more aggressive in Sasco than in Harlan SD rats (FIG. 1–3). Taken together, the array data appear to reflect what really happens in vivo in Sasco and Harlan SD rat carotid arteries in response to balloon vascular injury.

The data obtained in the present studies is consistent with previous investigations of restenosis. Two striking features of the data set derived from the current microarray experiments are, first, that genes upregulated in Harlan VSMCs have been implicated by other investigators in the prevention of restenosis and, second, that genes upregulated in Sasco VSMCs have been shown to play a role in pathogenesis of postangioplasty restenosis. For example, in the array system, the number of the cyclooxygenase 2 (COX-2) gene transcripts was almost 10-fold larger in restenosis-resistant Harlan VSMCs than in restenosis-prone Sasco VSMCs (Table 3). COX-2 produces prostacyclin, which functions through prostacyclin receptors. Prostacyclin receptor knockout mice have been shown to exhibit exaggerated restenosis in response to vascular injury[24], thereby supporting the protective role of prostacyclin against restenosis. Our array data also showed that the transcript number of monocyte chemoattractant protein-1 (MCP-1) gene was 3.36-fold larger in restenosis-prone Sasco VSMCs than in restenosis-resistant Harlan VSMCs (Table 2). MCP-1 is a chemokine produced by VSMCs in response to growth stimuli and a potent chemoattractant of monocytes. Recent studies indicated that higher plasma MCP-1 levels correlated with restenosis[25]. In addition, our array data indicated that the transcript of VCAM-1[26], Angiotensin-II receptors[27,28], tissue factor[29-31], P13K[32] and tenascin C[33], all of which have been strongly implicated in the pathogenesis of restenosis in animal studies, were all upregulated in restenosis-prone Sasco VSMCs (3.3, 9.0–12.8, 4.7, 11.2, and 3.4-fold increase, respectively) (Table 2). Taken together, these observations further support the validity of the current data set derived from our microarray experiments.

Another striking finding derived from the present investigations is that Harlan VSMCs appear to secrete several poorly characterized molecules into extracellular space. The four molecules BTG2, SBF, petraxin, and factalkine ($CX_3C$)

(PARIS-1 through -4, respectively), stand in clear contrast to molecules secreted by restenosis-prone Sasco VSMCs (Tables 3 and 4). The secreted molecules from Sasco VSMCs, including TGF-$\alpha^{34}$ and MCP-$1^{35}$ (Table 2), are well characterized and have been identified as contributors to restenosis. Just as restenosis-prone Sasco VSMCs secrete growth-promoting factors into their microenvironment, it is proposed that restenosis-resistant Harlan VSMCs secrete growth-limiting factors that negatively regulate the growth of neighboring VSMCs. These soluble and secreted growth-inhibitory molecules, named PARISs, are believed to be the molecules secreted by Harlan VSMCs that were hypothesized to be identifiable by microarray analyses of genes upregulated in Harlan VSMCs. The four representative PARISs identified herein are considered especially valuable for inhibiting cell proliferation. Further analysis is expected to identify more soluble secreted PARISs (e.g., PARIS-5, and so on), which may not be as highly expressed as PARISs 1–4 but nevertheless have useful biological activity which causes inhibition of cell growth. The term "highly expressed" means at least a 1.5-fold increase in expression of a PARIS protein in growing cells from a restenosis-resistant animal model compared to the level of expression of the same protein in growing cells from a restenosis prone animal model).

TABLE 2

GENES HIGHLY TRANSCRIBED IN SASCO SD VSMCS (20 OUT OF 32 GENES)

| Site of action | Gene family | Gene name | Accession | Hits | Fold | Ref. | Gene function and reference |
|---|---|---|---|---|---|---|---|
| Extracellular | Secreted protein, cytokine like | TGF-α | M31076 | 2 | 4.32 S | 1500 | Treatment with anti-sense oligos to TGF-α retarded cancer cell proliferation. Overexpression of TGF-α caused increased hepatocyte proliferation in transgenic mice. Involvement in restenosis likely. |
| | | MCP-1 | X17053 | 2 | 3.36 | 349 | MCP-1 is produced by VSMCs in response to PDGF and recruit monocytes. The role of MCP-1 in postangioplasty restenosis is clearly shown by multiple studies. |
| | Secreted protein, ECM | Tenascin C | U15550 | 1 | 3.42 S | 241 | Tenascin C is a matrix glycoprotein that plays a role in VSMC survival and proliferation. Involvement in restenosis likely. |
| | | F-spondin | M88469 | 1 | 11.18 S | 9 | F-spondin was initially reported as a secreted matrix protein that promoted neural cell adhesion, neurite extension, and and cartilage. MGP precursor is recently neuronal growth. |
| | | MGP | AI012030 | 1 | 3.63 | 59 | MGP is a 10 kDa matrix protein first described in bone, dentin discovered in VSMCs. |
| | | MEGF5 | AB011531 | 2 | 25.81 S | 5 | MEGF5 is a mammalian homolog of *Drosophila* slit protein. *Drosophila* Slit is a large ECM protein important in development. |
| Cell membrane | Adhesion molecule and analog | VCAM-1 | M84488 | 2 | 3.34 | 887 | VCAM induces PI3K activation and cell proliferation. Monoclonal antibody against VCAM inhibits neointimal formation, supporting the role of VCAM in restenosis. |
| | | Connexin | X51615 | 1 | 3.22 S | 707 | Connexin is a 21 kDa transmembrane protein, categorized as a gap-junction protein. It may have a potential anti-apoptotic function. |
| | Receptor | AT-II, type 1 | M86912 | 2 | 9.0 | 768 | Multiple studies have suggested the role of type 1 AT-II receptor in restenosis. |
| | | AT-II, type 2 | X62295 | 3 | 12.82 S | 1174 | Multiple studies have suggested the role of type 2 AT-II receptor in restenosis. |
| | | Tissue factor | U07619 | 1 | 4.72 | 1718 | Recombinant tissue factor inhibitor (rTFPI) prevents neointimal proliferation. Injured VSMCs express tissue factor on cell surface. |
| | | Oxidized LDL receptor (LOX1) | AB005900 | 1 | 8.88 | 47 | The receptor was originally found in endothelial cells but also later found also in VSMCs and macrophage. |
| Cytoplasmic | Housekeeping proteins | Guanine deaminase | AA859837 | 2 | 6.15 | 74 | Guanine deaminase is a 50 kDa protein that catalyzes the hydrolytic deamination of guanine. |
| | | Hydroxysteroid dehydrogenase 11β-type 1 | AI105448 | 1 | 4.86 | 366 | Hydroxysteroid dehydrogenase converts cortisone (less glucocorticoid activity) into cortisol (more glucocorticoid activity). |
| | | Glycogenin-homolog | AA892986 | 1 | 13.09 | 56 | Glycogenin is a 42 kDa protein required for the initiation of glycogen biogenesis. |
| | | Aldehyde dehydrogenase | U60063 | 2 | 8.06 S | 1354 | Lack of aldehyde dehydrogenase causes the clinical pictures of Sjogren-Larsson syndrome with muscular dystrophy. |
| | | VDUP1 | AI237654 | 2 | 4.38 | 3 | VDUP1 was originally cloned as a protein interacting with thioredoxin. VDUP1 is upregulated in immortalized cells but not present in cell-cycle arrested cells |
| | Regulatory, Kinases | Phosphoinositide-3-kinase(PI3K) | U50412 | 3 | 11.24 S | 1903 | PI3K plays a critical role in the proliferation of all cell types, including VSMCs. |
| | Regulatory, Signaling mol | cAMP-PDE | M25350 | 5 | 4.72 S | 415 | There is a report that PDE inhibitors, such as aminophyline and amrinone, prevented restenosis. |

TABLE 2-continued

GENES HIGHLY TRANSCRIBED IN SASCO SD VSMCS (20 OUT OF 32 GENES)

| Site of action | Gene family | Gene name | Accession | Hits | Fold | Ref. | Gene function and reference |
|---|---|---|---|---|---|---|---|
| | Regulatory, Survival | NDRG2 | AA799560 | 1 | 4.26 | 13 | NDRG2 is 47 kDa protein upregulated by N-myc, related to cell survival and proliferation. |

Legends:
Accession: Accession number at GenBank;
Fold: The signal intensity of a certain gene is X-fold elevated in Sasco in comparison with Harlan SD VSMCs;
S: Transcript only present in Sasco SD VSMCs;
Ref.: The number of articles appearing in MedLine search;
TGF-α: Transforming growth factor-α;
MCP-1: Monocyte chemoattractant protein-1, also known as JE rat immediate-early serum-responsive gene;
ECM: Extracellular matrix;
MGP: Matrix Gla protein;
MEGF5: Mammalian homolog of *Drosophila* slit protein with EGF (epidermal growth factor) domains;
VCAM-1: Vascular cell adhesion molecule-1;
AT-II: Angiotensin-II receptor;
VDUP1: Upregulated by 1,25-dihydroxyvitamin D3;
PDE: Phosphodiesterase;
NDRG2: N-myc downstream-regulated gene-2 homolog, also known as Bdm1 in rat and Ndr1-3 in mouse.

TABLE 3

GENES HIGHLY TRANSCRIBED IN HARLAN SD VSMCS (18 OUT OF 34 GENES)

| Site of action | Gene family | Gene name | Accession | Hits | Fold | Ref. | Gene function and reference |
|---|---|---|---|---|---|---|---|
| Extracellular | Secreted protein, cytokine like | BTG2 (PARIS3) | M60921 | 3 | 4.0 | 8 | Also known as B cell translocation gene, anti-proliferative and secreted. Induced by p53. |
| | | SBF gene (MIC-1, (PARIS2) | AJ011969 | 1 | 3.67 H | 8 | SBF gene is a poorly characterized secreted protein whose function is unknown. |
| | | Neuronal Pentraxin (PARIS1) | AI072943 | 1 | 6.59 H | 6 | Neuronal pentraxin is a 47 kDa secreted protein, homologous to C-reactive protein and amyloid P protein. Overexpression of pentraxin was associated with apoptosis in one report. |
| | | CX3C (Fractalkine; PARIS4) | AF030358 | 1 | 5.06 | 72 | CX3C was originally characterized as chemoattractant for T cells and monocytes. One report indicated it to be induced by p53. |
| | Secreted protein, ECM | Small proline-rich protein (spr) | AA891911 | 1 | 3.46 | 6 | Spr is a 120 kDa proline rich protein, originally described in human skin. |
| Cell membrane | Adhesion molecule | H36-alpha7 integrin α-chain | X65036 | 2 | 3.78 H | 1 | This is a newly described 120 kDa cell surface glycoprotein that binds lamin. |
| | Vesicle transportation | Caveolin-3 | AI043968 | 2 | 6.68 H | 43 | Caveolin-3 is a muscle specific caveolae also present in VSMCs. |
| | Channel | P2X5 | X92069 | 2 | 6.82 H | 6 | P2X5 is a component of ligand-gated ion-channel family of ATP receptor. It makes a heterodimer with P2X1. |
| | | MCT2 | U62316 | 1 | 3.43 | 1 | MCT2 transports pyruvate and lactate across cellular membrane. |
| Cytoplasmic | Cytoskeleton | γ-2 smooth muscle cell actin | M22323 | 4 | 4.26 H | 6 | γ-2 actin is normally present in enteric smooth muscle cells. |
| | | Cytokeratin-18 | AI072634 | 2 | 11.24 H | 36 | Cytokeratin-18 is a cytoskeleton and cytosolic protein. Upon apoptosis, the protein is cleaved and released into the blood stream, exhibiting a new epitope detectable by M30 monoclonal antibody. |
| | | Smooth muscle, MHC-AS | X16262 | 2 | 9.45 H | 189 | Smooth muscle MHC-AS is a splicing variant of MHC. |
| | | b-Nexillin | AA799423 | 2 | 3.58 | 1 | b-Nexillin is a cytoskeleton protein that interacts with F-actin and involved in cell-matrix adhesion. |
| | Regulatory molecules | Guanylate cyclase 1 | AA849036 | 3 | 10.48 H | 259 | Guanylate cyclase 1 produces cGMP, an intracellular signaling molecule, in response to NO. NO prevents neointimal proliferation in animal model of restenosis. |
| | | Cyclooxigenase isoform 2 | S67722 | 3 | 9.58 H | 655 | COX-2 produces prostacyclin. Prostacyclin receptor KO mice have aggressive neointima proliferation. |
| Nuclear | Transcriptional factor | HES-1 | D13417 | 3 | 6.68 H | 25 | HES-1 is a helix-loop-helix protein, functioning as a transcriptional repressor. Overexpression of HES-1 has been found associated with reduction of PCNA level and cell cycle arrest. |
| | | Calbindin-D28k (CCBPS35P) | AI102839 | 2 | 3.9 H | 205 | Calb1 is Notch 3 homolog. Notch 1 function as the enhancer of HES-1. Involved in HES-1 pathway. |

TABLE 3-continued

GENES HIGHLY TRANSCRIBED IN HARLAN SD VSMCS (18 OUT OF 34 GENES)

| Site of action | Gene family | Gene name | Accession | Hits | Fold | Ref. | Gene function and reference |
|---|---|---|---|---|---|---|---|
| | | HMG1 | X62875 | 1 | 3.25 | 26 | HMG1 is a 26 kDa nuclear nonhistone DNA binding protein, interacting with histone proteins. One group showed HMG1 is a p53 activator. |

Legends:
Accession: Accession number at GenBank;
Fold: The signal intensity of a certain gene is X-fold elevated in Harlan in comparison with Sasco SD VSMCs;
H: Transcript only present in Harlan SD VSMCs;
Ref.: The number of articles appearing in MedLine search;
GdNPF: Glia-derived neurite-promoting factor;
EST: Expressed sequence tag;
NGFIAPPSP: NGF-inducible anti-proliferative putative secreted protein;
ECM: Extracellular matrix;
MCT2; Monocarboxylate transporter;
MHC-AS; Myosin heavy chain, alternatively spliced;
CCBPS35P; Cerebellar Ca-binding protein spot 35 protein, also known as Calb1;
HMG1: High mobility group protein 1.

TABLE 4

IDENTIFICATION OF PARISs 1–4

| Name | Other name(s) | Homology, Family | Implicated function | Fold-inc. | Size | HRI | CVSE | GenBank | SP |
|---|---|---|---|---|---|---|---|---|---|
| PARIS-1 | Neuronal pentraxin 1 | Amyloid P protein | Pro-apoptosis? | 6.59 | 431aa | 88% | Yes | U18772 | Yes |
| PARIS-2 | SBP (MIC-1, GDF-15) | TGF-β superfamily | Anti-inflammatory? | 3.67 | 224aa | 56% | Yes | NM_019216 | Yes |
| PARIS-3 | BTG2 | Unknown | Anti-proliferative? | 4.0 | 158aa | 83% | Yes | M60921 | Yes+ |
| PARIS-4 | Fractalkine, soluble | $CX_3C$ chemokine | Anti-adhesion? | 5.06 | 393aa | 63% | Yes | AF030358 | Yes |

Legend:
HRI: Human-rat identity at the protein level.
Size: the number of amino acids in rat proteins;
CVSE: Cardiovascular system expression, defined by EST database was searched, literature reviewed.
GenBank: GenBank accession number for rat mRNA sequence;
SP: Signal peptide sequence present. This was tested using SIGFIND[64] an internet based Signal peptide prediction software that has been described by Reczko et al.[62];
+Negative by this server but signal peptide described by Badbury[65] and others.

TABLE 5

PARISs 1–4 SEQUENCES

| Name | Human Protein | Common | PARIS-1 Neuronal pentraxin I precursor | PARIS-2 Prostate differentiation factor | PARIS-3 BTG2 | PARIS-4 Fractalkine |
|---|---|---|---|---|---|---|
| | | Others | NPX-1 | MIC-1, PLAB, GDF-15 | NGF-inducible protein, TIS21, Nerve growth factor-inducible protein PC3 precursor | Neurotactin, small inducible cytokine subfamily D, CX3CL1 |
| Amino Acid | Accession Number | *H. sapiens* | Q15818 | NP_004855 | P78543 | NP_002987 |
| | | *M. musculus* | Q62443 | Q9Z0J7 | Q04211 | O35188 |
| | | *R. norvegicus* | P47971 | Q9Z0J6 | A40443 | O55145 |
| | Sequence | *H. sapiens* | [SEQ ID NO: 1] MPAGRARTCAL LALCLLGPQD FGPTRFICTSV PVDADMCAAS VAAGGAEELRS SNVLQLRETV LQQKETILSQK ETIRELTAKLG LQQKETILSQKE TIRELTAKLG RCESQSTLDP GAGEARAGGGR KQPGSGKNTMG DLSRTPAAET LSQLGQTLQSL KTRLENLEQY SRLNSSSQTN SLKDLLQSKIDE | [SEQ ID NO: 2] MPGQELRTVN GSQMLLVLLVS WLPHGGALSLA EASRASFPGPSE LHSEDSRFRELRKR YEDLLTRLR ANQSWEDSN TDLVPAPAVRILTP ANQSWEDSNT DLVPAPAVRILTP EVRLGSGGHLHLR ISRAALPEGL PEASRLHRALFRLS PTASRSWDV TRPLRRQLSLARP QAPALHLRLS PPPSQSDQLL AESSSARPQLELHL | [SEQ ID NO: 3] MSHGKGTDMLP EIAAAVGFLSS LLRTRGCVSE QRLKVFSGALQE ALTEHYKHHWFPE KPSKGSGY RCIRINHKMDPIIS RVASQIGLSQ RCIRINHKMDPIIS RVASQIGLSQ PQLHQLLPSELTL WVDPYEVSY RIGEDGSICVLYEE APLAASCGL LTCKNQVLLGRSS PSKNYVMA VSS | [SEQ ID NO: 4] MAPISLSWLLR LATFCHLTVLLA GQHHGVTKCNIT CSKMTSKIPVA LLIHYQQNQAS CGKRAIILETRQH RLFCADPKEQWV KDAMQHLDR RLFCADPKEQWV KDAMQHLDR QAAALTRNGGT FEKQIGEVKPRT TPAAGGMDESVVL EPEATGESSS LEPTPSSQEAQRA LGTSPELPTGV TGSSGTRLPPTP KAQDGGPVGTE |

TABLE 5-continued

PARISs 1-4 SEQUENCES

| Name | Human Protein | Common | PARIS-1 Neuronal pentraxin I precursor | PARIS-2 Prostate differentiation factor | PARIS-3 BTG2 | PARIS-4 Fractalkine |
|---|---|---|---|---|---|---|
| | | | LERQVLSRVNTL | RPQAARGRRRAR | | LFRVPPVSTAAT |
| | | | EEGKGGPKN | ARNGDDCPLG | | WQSSAPHQPGP |
| | | | DTEERVKIETA | PGRCCRLHTVR | | SLWAEAKTSEA |
| | | | LTSLHQRISELE | ASLEDLGWAD | | PSTQDPSTQAST |
| | | | KGQKDNRPGDK | WVLSPREVQVTM | | ASSPAPEENAPSEG |
| | | | FQLTFPLRTN | CIGACPSQFR | | QRVWGQGQS |
| | | | YMYAKVKKSL | AANMHAQIKT | | PRPENSLEREEM |
| | | | PEMYAFTVCM | SLHRLKPDTEPA | | GPVPAHTDAFQ |
| | | | WLKSSATPGVG | PCCVPASYNPM | | DWGPGSMAHVS |
| | | | TPFSYAVPGQ | VLIQKTDTGVSL | | VVPVSSEGTPSR |
| | | | ANELVLIEWGN | QTYDDLLA | | EPVASGSWTPK |
| | | | NPMEILINDK | KDCHCI | | AEEPIHATMDPQ |
| | | | VAKLPFVIND | | | RLGVLITPVPDAQ |
| | | | GKWHHICVTWT | | | AATRRQAVGL |
| | | | TRDGVEAYQDG | | | LAFLGLLFCLG |
| | | | TQGGSGENL | | | VAMFTYQSLQGC |
| | | | APYHPIKPQG | | | PRKMAGEMAE |
| | | | VLVLGQEQDTL | | | GLRYIPRSCGSNS |
| | | | GGGFDATQAFV | | | YVLVPV |
| | | | GELAHFNIWD | | | |
| | | | RKLTPGEVYNLA | | | |
| | | | TCSTKALSGNV | | | |
| | | | IAWAESHIEIYG | | | |
| | | | GATKWTFEAC | | | |
| | | | RQIN | | | |
| mRNA | Accession Number | H. sapiens | U61849 | NM_004864 | U72649 | NM_002996 |
| | | M. musculus | NM_008730 | NM_011819 | AK088976 | AF071549 |
| | | R. norvegicus | U18772 | NM_019216 | M60921 | AF030358 |

EXAMPLE 6

Identification of PARISs 1-4

To simplify this discussion, the representative molecules that were identified as described in the foregoing examples through microarray screening as potential negative regulators of VSMC growth are called PARISs 1-4. The name "PARIS" is an acronym derived from the phrase "protein associated with restenosis inhibition and secreted." Additional identifying information and properties of these molecules are listed in Tables 4 and 5. In Table 4 the homology or protein family of each of the four proteins is identified, along with its implicated function. The fold increase in expression, number of amino acids and percent human-rat identity are shown. The GenBank accession number for the rat mRNA sequence of each PARIS 1-4 are also indicated in Table 4. The GenBank accession numbers of the amino acid and mRNA sequences PARISs 1-4 from human, mouse and rat are given in Table 5. The sequences referenced by those accession numbers are hereby incorporated herein by reference. The amino acid sequences for human PARISs 1-4 are also set out in the attached Sequence Listing as SEQ ID NO:1, SEQ ID NO:2, SEQ ID NO:3 and SEQ ID NO:4.

The identification of PARISs represents a new paradigm because a negative growth-regulatory mechanism of VSMCs by secreted molecules has never been well elucidated and because none of the molecules mentioned above has ever been implicated before in the growth regulation of VSMCs. It should be appreciated that the elucidation of secreted negative regulators of VSMC growth constitutes a significant advance in the prevention and treatment of restenosis. Although it is possible to treat restenosis by blocking the effect of soluble growth-promoting molecules (such as MCP-1, TGF-α, PDGF, and others) by abolishing their binding to their receptors or by inhibiting their intracellular signal transduction pathways, using small molecules or antibodies, these approaches are complex and time-consuming. In contrast, when fully characterized and validated, the secreted negative regulators of VSMC growth, as represented by those molecules identified herein, are expected to be suitable for simple parenteral or local administration to prevent restenosis. Advantageously, there should be little or no toxicity because they are naturally occurring molecules.

The four representative PARISs range in size from 17 to 47.4 kDa (predicted). As indicated in Table 4, the human PARISs 1-4 are orthologs of the rat PARISs, having very close amino acid sequences (i.e., human/rat identities ranging from 56-88%.) Additional exemplary orthologs are identified in Table 7. Since PARISs 1-4 were originally identified in transcripts from pure cultured VSMCs, the inventors considered their presence in the cardiovascular system is likely. In fact, recent Northern and Western blot analyses confirmed the presence of PARIS-4 in cardiovascular tissue. It was also concluded in this study that putative signal peptide sequences were present. In the following paragraphs, the properties of PARIS 1-4 are described.

PARIS-1

The sequence originally identified as AI072943 (EST sequence) represents a 364-nucleotide cDNA fragment. A BLAST search showed a 100% match with the 3-terminus untranslated region of neuronal pentraxin-1 (GenBank Acc. No. U18772). The rat neuronal pentraxin-1 was originally identified as a 47-kDa protein that binds to the snake venom toxin taipoxin. Structurally, neuronal pentraxin-1 is homologous to the acute-phase proteins serum amyloid P protein and C-reactive protein of the pentraxin family[36]. Neuronal pentraxin-2, which has 54% amino acid identity to neuronal pentraxin-1, has been cloned by library screening using neuronal pentraxin-1 as a probe[37]. Both proteins are apparently secreted, since they can both be detected in conditioned media by Western blot analysis[38]. Recently, neuronal pentraxin-1 was shown to be upregulated, both at the transcript and protein levels, in cerebellar granule cells undergoing potassium deprivation-induced cell death[39]. When the cells were treated with antisense oligonucleotides directed against neuronal pentraxin-1, more cells survived upon potassium deprivation, further supporting the protein's role in negative growth regulation and cell death[39]. It appears that no other functional study of this molecule using either recombinant protein or overexpression strategies has ever been performed. A Medline search revealed only 6 articles that used neuronal pentraxin in their titles, however none of which indicates negative growth regulatory function. Overall, this protein has not previously been well characterized.

PARIS-2

The sequence originally identified as AJ 011969 (EST sequence) represents the cDNA of the rat MIC-1 protein. This protein is also known as SBP and GDF-15 (GenBank Acc. No. NM_019216). MIC-1 was originally identified by subtraction cloning as a molecule that is upregulated in phorbol-12-myristate-13-acetate-(PMA)-stimulated U937 cells as opposed to retinoic acid (RA)-differentiated U937 cells[40]. Structurally, MIC-1 is remotely homologous to TGF-β[40]. This protein is apparently secreted, since FLAG-epitope-(DYKDDDDK)-tagged MIC-1, when overexpressed in CHO cells, is successfully immunoprecipitated from conditioned media by anti-FLAG antibody[40]. Although the processing, secretion, and degradation pathway of MIC-1 has been fairly well investigated[41], there has been no scientifically sound functional study done on this molecule. TGF-β1-knockout mice die of severe widespread inflammation[42], suggesting that one of the major functions of the TGF-β family is the negative regulation of inflammation. Taken together, these data suggest that the function of MIC-1 is also anti-inflammatory. A Medline search revealed only 10 articles that used MIC-1, SBP, or GDF-15 in their titles, none of which clearly shows its growth inhibitory function. Overall, this protein is very poorly characterized.

PARIS-3

The sequence identified as M60921 represents the cDNA of the rat BTG-2 protein. This protein is also known as TIS21, PC3, and NGF-inducible anti-proliferative putative secreted protein. BTG-2 was originally cloned as a molecule whose transcription is induced by nerve growth factor (NGF) stimulation of PC12 pheochromocytoma cells[43]. Overexpression of this protein has never been performed in tissue culture cell system. BTG-2 protein reportedly interacts with proteins of various functions, including protein-kinase-Cα-binding protein (rPICK1)[44], protein-arginine N-methyltransferase[45], and CCR4-associated factor 1 (CAF1)[46]. In addition, intracellular localization of BTG-2 has never been clearly shown, despite the presence of signal peptide sequence. Its function in negative growth regulation is vaguely implied by the fact that BTG-depleted cells are less susceptible to Adriamycin challenge and the fact that BTG-overexpressing cells are growth-suppressed[47]. A Medline search revealed only 23 articles that used BTG-2, TIS, PC3 or NGF-inducible anti-proliferative putative secreted protein in their titles. No previous studies definitively show its role in negative growth regulation. Overall, this protein is poorly characterized.

PARIS-4

The sequence identified as AF030358 represents the cDNA of the rat fractalkine protein. Fractalkine is also known as the $CX_3C$ chemokine. This protein is unique because even though it is expressed on the cell surface, its N-terminus chemokine head can be cleaved from a mucin stalk[48]. Fractalkine is expressed on various cells including endothelial cells, VSMCs, and dendritic cells, while its receptor ($CX_3CR1$) has been so far demonstrated on T cells, monocytes, macrophages, and natural killer cells[49]. Its expression is upregulated by TNF-α and IL-β[50]. Fractalkine has different functions, depending on its form: membrane-bound fractalkine is implicated in integrin-independent leukocyte migration[48], while soluble fractalkine is an anti-inflammatory agent that interferes with the ligation of membrane-bound fractalkine to its receptor on the leukocyte surface[51,52]. It is especially interesting to note that a group of investigators has been able to show the attenuation of THP-1 cell adhesion to activated VSMCs by soluble fractalkine (50 nM)[53]. It is now proposed that fractalkine expressed on VSMCs may be cleaved under certain circumstances and play a role in the attenuation of inflammation. A Medline search revealed 72 articles that used fractalkine or $CX_3C$ in their titles. Only one paper investigated VSMCs and fractalkine[53]. Overall, the role of fractalkine in VSMC growth is poorly characterized and no previous work clearly demonstrated its negative regulatory function with respect to cell growth. For the sake of simplicity and because of the functional difference between soluble and membrane-bound fractalkine, it is the extracellular domain of fractalkine (i.e. soluble fractalkine) that is defined herein as PARIS-4.

EXAMPLE 7

Initial Validation and Characterization of PARISs

After identifying the first four PARISs, as described in the foregoing Examples, one was chosen as a representative for examination in a series of experiments designed to test the hypothesis that proliferating VSMCs secrete PARISs, chemokine-like molecules that negatively regulate the growth of neighboring VSMCs could be supported in that PARIS. Because some of the key reagents needed to test the hypothesis were already available in the inventors' laboratory for PARIS-4, it was decided to begin with PARIS-4. In brief, the rationale was that, if PARIS-4 produced by VSMCs did inhibit VSMC growth under carefully defined assay conditions, then it could be concluded that the other PARISs discovered using the same methods will very likely behave similarly in accordance the general hypothesis. The experimental data establishes that PARIS-4 is, in fact, produced by VSMCs, and that PARIS-4 causes VSMCs to grow more slowly than in the absence of PARIS-4.

Figure 14:
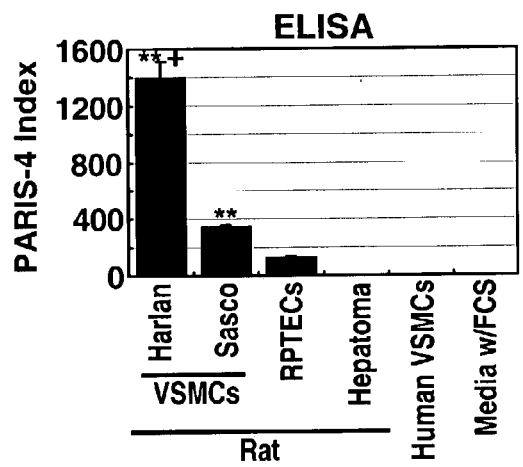
FIG. 14 is a bar graph showing the results of an ELISA analysis of rat PARIS-4 protein in Harlan VSMCs, Sasco VSMCs, rat proximal tubule epithelial cells (RPTECs), hepatoma, human VSMCs and plain media with fetal calf serum.

Accordingly, the following discussion and experimental data focus primarily on PARIS-4 (soluble fractalkine), and is considered to be representative of PARISs 1–3 as well as any as yet unidentified soluble secreted proteins that are also highly expressed in growing vascular smooth muscle cells. In brief, it was determined that PARIS-4 is in fact secreted from vascular smooth muscle cells (FIGS. 8 and 14). In addition, it was found that PARIS-4 production is much more robust in vascular smooth muscle cells from restenosis resistant rat substrains (Harlan SD rats) (FIGS. 15A–C and 16). Furthermore, it was demonstrated that the addition of recombinant PARIS-4 to vascular smooth muscle cell culture will slow the growth rate of vascular smooth muscle cells (FIG. 17). In ongoing work, a large amount of PARIS-4 is currently being produced and additional in vivo confirmation that this molecule will prevent post-angioplasty restenosis in a rat carotid-artery model of restenosis (FIGS. 18A–D) is planned.

Real-Time RT-PCR Analysis

Figure 11:
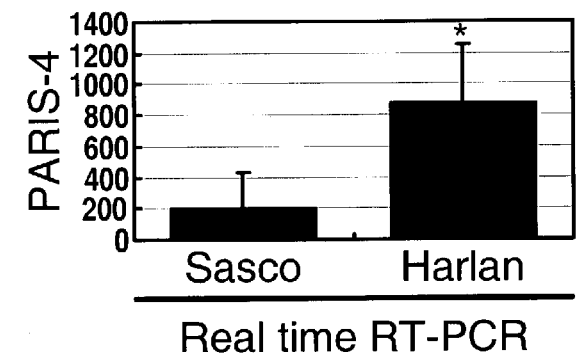
FIG. 11 is a bar graph comparing the real time RT-PCR, showing the up-regulation of PARIS-4 mRNA (ng) in growing Harlan VSMCs compared to Sasco VSMCs.

A real-time RT-PCR analysis was developed for the quantitation of PARIS-4 messages in Harlan and Sasco carotid artery VSMCs. The results are shown in FIG. 11. PARIS-4 (Y-axis) represents PARIS-4 index, which is PARIS-4 mRNA (ng) normalized to 18S eukaryotic RNA (ng). Asterisk denotes P<0.05.

The experimental protocol was as follows: VSMCs from the carotid arteries of 4 Sasco and 4 Harlan rats were used. When VSMCs on 10-cm dishes were 80% confluent, cells were harvested. The total RNA were extracted using a RNeasy Midi kit (Qiagen). The real time RT-PCR was performed according to the instructions from Applied Biosystems (Foster City, Calif.), using the following primer and probe sets for the detection of PARIS-4 (rat fractalkine) transcripts:

```
forward primer,   5'-TACTCTGCTGGCGGGTCAG-3';
reverse primer,   5'-ATCTTGTGGCACGTGATGTTG-3';
probe,            5'-ACCTCGGCATGACGAA-3'.
```

The probe was labeled at the 5'-end with 6-carboxyl-fluorescein (FAM™) and at the 3'-end with a 6-carboxytetramethylrhodamine (TAMRA™). For the detection of eukaryotic 18S RNA for normalization, the pre-developed assay mixture for 18S, consisting of appropriate primers and probe labeled by VIC™ and non-fluorescent quencher (PDAR, ABI) was used. The quantitative real time RT-PCRs were performed in quadruplicate, using the TaqMan RT-PCR kit (ABI) in the 7900 HT Sequence Detector system. Both PARIS-4 and 18S critical thresholds were determined and converted to weight (ng) using a standard curve constructed on serially diluted rat normal total RNA. PARIS-4 index was then calculated as above. It is readily apparent in FIG. 11 that there is up-regulation of PARIS-4 message in Harlan VSMCs. The PARIS-4 message in Harlan VSMCs was 4 times more abundant than in Sasco VSMCs.

Northern Blot Analysis of Rat PARIS-4

Figure 12:
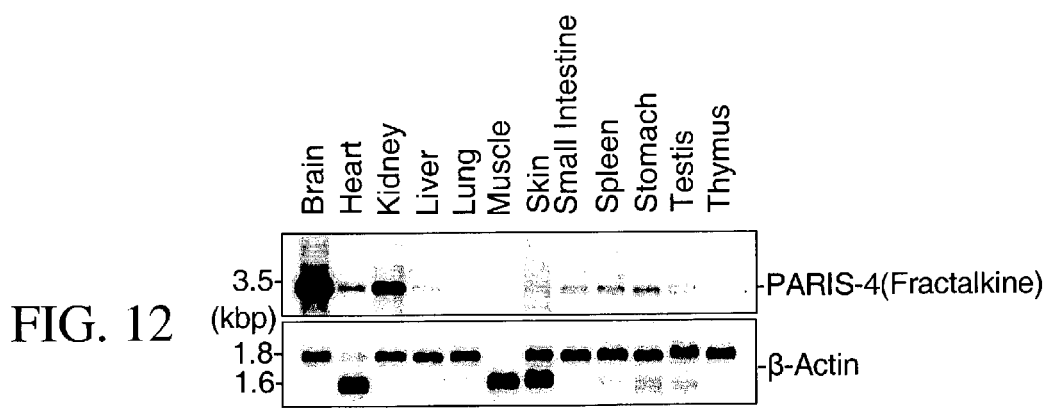
FIG. 12 is a photograph of a Northern blot analysis of rat PARIS-4 mRNA showing its relative concentration in various rat tissues.

Referring now to FIG. 12, the results of a Northern blot analysis of rat PARIS-4 (Fractalkine) are shown. The method was as follows: Rat PolyA+ RNA blot was purchased from OriGene Technologies (Rockville, Md.). PARIS-4 cDNA was cloned by RT-PCR from total RNA isolated from Harlan VSMCs and ligated in frame to a pBlueBac4.5 vector (Invitrogen) and subjected to automated DNA sequencing. Labeling of probes (PARIS-4 and β-actin) were performed using Random Prime kit (Roche) with gel purified PCR products of PARIS-4 and β-actin as templates and with $^{32}$-α-dCTP as a labeling agent. Generated probes were purified using a Qiagen nucleotide clean up kit. Hybridization was performed at 60° C. for 16 hrs in ExpressHyb solution. The membrane was then washed 5 times with 2×SSC with 0.1% SDS at room temperature and twice with 1×SSC with 0.1% SDS at 50° C. before it was exposed to a phosphoimager screen for 8–12 hrs. Signals were detected by BiORad Molecular Scanner FX and Quantity One software system. The Northern blot analysis showed PARIS-4 to be abundant in brain, kidney and heart. In FIG. 12 kbp refers to kilo-base pairs. The rich presence of PARIS-4 in the heart is consistent with the hypothesis that PARIS-4 is involved in the growth regulation of cells in cardiovascular tissue and, in particular, VSMCs.

Western Blot Analysis of PARIS-4

Figure 13:
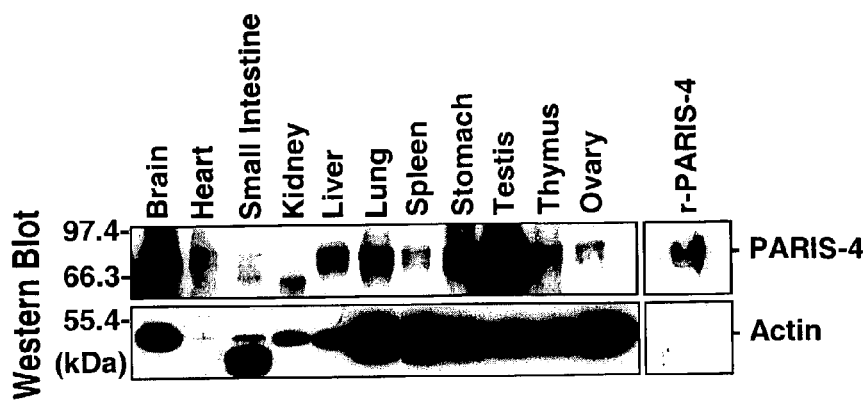
FIG. 13 is a photograph of a Western blot analysis of rat PARIS-4 protein showing its relative expression in various rat tissues.

A commercially available antibody suited for PARIS-4 Western blot was identified and used to evaluate the expression of PARIS-4 protein in various tissues. Results are shown in FIG. 13, in which kDa denotes kilo Dalton, and r-PARIS-4 indicates recombinant PARIS-4. Western blot analysis of rat PARIS-4 (Fractalkine) shows its abundant presence in brain, heart, liver and testis.

The assay protocol was as follows: A ready-made rat tissue blot, containing 10g per lane of different rat tissue lysates were purchased from Imgenex (San Diego, Calif.). Western blot analysis was performed using a standard technique with mouse anti-rat fractalkine antibody (Clone 96834) from R&D Systems, Inc. (1:500 dilutions). Bound antibodies were detected using anti-mouse IgG-horse-raddish-peroxidase (HRP)-conjugates and West Pico HRP substrates (Pierce, Rockford, Ill.). In order to evaluate the loading condition of the samples, the same membrane was probed with anti-actin antibody (Chemicon, Temecula, Calif.). Recombinant PARIS-4 was used as positive control (r-PARIS-4, FIG. 13). Evaluation of the signals of PARIS-4 and actin (including normalization to the total actin amounts) suggests that PARIS-4 is highly expressed in brain, heart, testis and liver. Of particular note, brain and heart are the only organs that showed high levels of PARIS-4 both transcripts and proteins. In the kidney, PARIS-4 protein expression was only modest while its transcript was abundant. In the testis and liver, PARIS-4 protein expression was large in quantity while its transcript was minimally present. The concordant presence of PARIS-4 transcript and protein in the heart further supports the proposition that PARIS-4 plays an important regulatory role in cardiovascular cells.

ELISA Analysis of PARIS-4

Next, an ELISA system for PARIS-4 was developed and optimized using commercially available reagents (R&D Systems). The protocol was as follows: 96-well plates were coated with 0.8 μg/mL of goat anti-rat fractalkine antibody (R&D systems) overnight. After wash, plates were blocked with PBS supplemented with 1% BSA and 5% sucrose for 1 hr. After wash, 100 μL of samples or standards were added in quadruplicate and incubated for 2 hrs at room temperature (RT). After extensive wash, 100 μL of biotinylated goat anti-rat fractalkine antibody (0.3 μg/mL) was added and incubated for 2 hrs at RT. After wash, 100 μL of streptavidin-HRP solution was added and incubated for 20 min at RT. After wash, 100 μL of substrate solution ($H_2O_2$ plus tetramethylbenzidine) was added and incubated for 20 min. Stop solution was then added (2N $H_2SO_4$). And plates were read using a micro-plate reader set to 450 nm with a reference at 570 nm. Experiments were performed at least 3 times and results were essentially identical. The results are shown in FIG. 14, in which ** indicates P<0.001 in comparison with RPTECs; +indicates P<0.001 in comparison with Sasco; RPTECs indicates renal proximal tubule epithelial cells; and FCS indicates fetal calf serum. Notably, PARIS-4 concentration of media, determined by this system, was zero. In addition, PARIS-4 was not detectable in the conditioned media from human aorta vascular smooth muscle cells, suggesting the anti-rat primary antibody did not cross react with human fractalkine (i.e., the anti-rat antibody was capable of differentiating human from rat fractalkine). It was also found that fetal calf serum (FCS) did not contain detectable PARIS-4, as shown in FIG. 14. Rat Harlan and Sasco VSMCs secreted, respectively, approximately 10 fold and 3 fold as much PARIS-4 as rat renal proximal tubule epithelial cells (RPTECs), consistent with the data presented in FIG. 13.

EXAMPLE 8

Demonstration of More Rapid Production of PARIS-4 in Harlan VSMCs

Using the above-described ELISA system, it was found that Harlan conditioned media had two times more PARIS-4 than did Sasco conditioned media, as shown in FIGS. 15A-C. FIG. 15A shows the PARIS-4 concentration from condition media of 24 hr incubation; FIG. 15B: PARIS-4 from conditioned media of 48 hr incubation; FIG. 15C: PARIS-4 secretion rate (/hr). Asterisk denotes P<0.05. #: P=0.060, %: P=0.054. PARIS-4 index was obtained by normalizing concentration of PARIS-4 (ng/mL) to cell number (million). The ELISA protocol was as described in Example 7.

Figure 15:
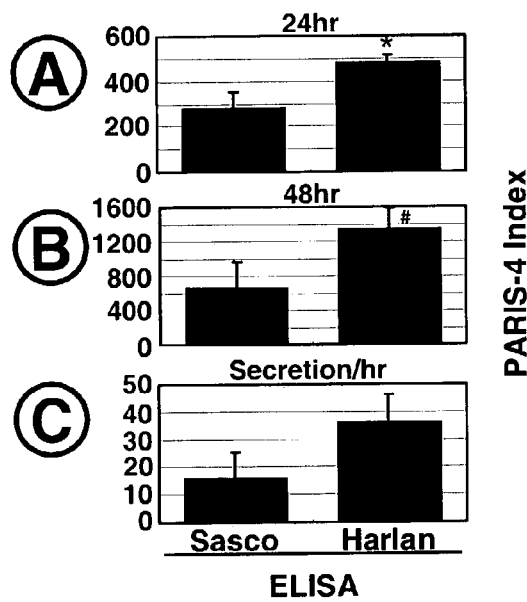
FIGS. 15A–C are bar graphs comparing the amount of PARIS-4 protein found in the conditioned media of Harlan VSMCS and Sasco VSMCs.
Figure 16:
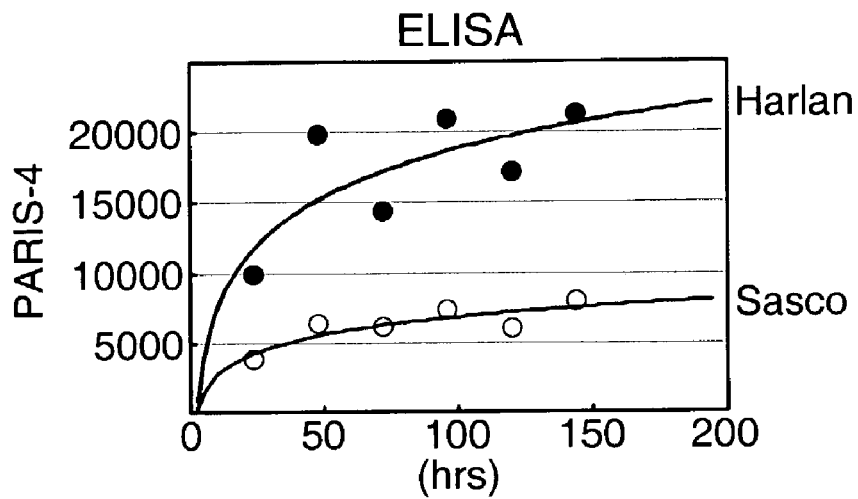
FIG. 16 is a graph showing PARIS-4 production by growing Harlan and Sasco VSMCs over a 200 hr. period in cell culture.
Figure 17:
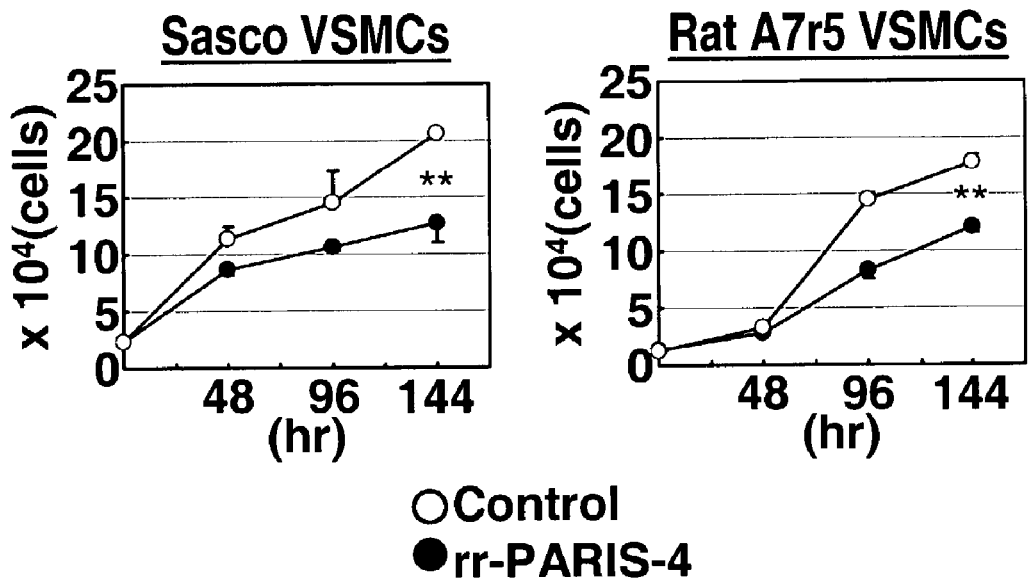
FIG. 17 is a pair of graphs showing cell growth in the presence or absence of recombinant rat PARIS-4. (Left panel) Sasco VSMCs. (Right panel) Rat A7r5 VSMCs.

Referring now to FIG. 16, the results of a cell growth time course experiment are shown. The protocol was as follows: 0.5 million Harlan and Sasco VSMCs were seeded on each well of 6 well dishes with 3 mL Media 231 with growth supplements. Time 0, 24, 48, 72, 96, 120 and 144 hrs after the exchange of media, 350 μL of media was harvested and the same volume of fresh media added. ELISA of PARIS-4 was performed in triplicate as described above. The time course experiment revealed more abundant and more rapid production of PARIS-4 by Harlan VSMCs than by Sasco SD VSMCs under the same conditions. PARIS-4 concentrations (ng/mL/million cells) were significantly higher for times 48, 72, 122, and 144 hrs (P<0.05, 2 Sample-T test) with strong trends for times 24 and 96 hrs (P=0.094 and 0.063, respectively). Overall, PARIS-4 concentration was significantly higher in Harlan than in Sasco (F=50.0, ANOVA, P<0.0001). PARIS-4 production was more rapid in the first 24–48 hrs than later hours. In addition, time course experiments showed that VSMCs produced PARIS-4 more rapidly in the first 24 hrs than later hours (FIG. 16) and that Harlan VSMCs secreted more PARIS-4 per hour than did Sasco VSMCs (FIGS. 15-C and 16). These data suggest that PARIS-4 protein is more rapidly and more abundantly secreted by Harlan VSMCs. Taken together, they very strongly support the validity of microarray and real-time RT-PCR data (for the PARIS-4 transcripts) at the protein level.

As discussed above, VSMCs grow much more slowly in Harlan conditioned media than in Sasco conditioned media. VSMCs from Sasco SD rats grew much more slowly in Harlan conditioned media rich in PARIS-4, as shown in FIG. 8A. Sasco, not Harlan VSMCs, were chosen for this assay because Harlan VSMCs rapidly produced PARIS-4 and would suppress their own growth, as made clear in FIGS. 15 and 16. This fact explains the lack of significant difference in growth rates of Harlan VSMCs in the exact same experiments (data not shown).

EXAMPLE 9

Inhibition of VSMC Growth by Recombinant PARIS-4

Cell growth assays were carried out to evaluate the effect of addition of PARIS-4 to growing VSMCs. The protocol was as follows: $1 \times 10^4$ cells (either Sasco VSMCs or A7r5 VSMCs [ATCC]) were seeded on 6-well plates in duplicate. Next day, media were exchanged for media either containing recombinant rat PARIS-4 (fractalkine) at the final concentration of 10000 ng/mL (140 nM) or the same volume of PBS. The number of cells in each well was determined every 48 hours for 6 days. Graphs of the results are shown in FIGS. 17A–B. Double asterisks denote P<0.001 by ANOVA (General linear model). Error bars denote standard deviations (SD). Hr denotes hours after the addition of r-PARIS-4. FIG. 17A shows Sasco VSMC cell number after 48, 96 and 144 hours culture, with or without recombinant rat PARIS-4. FIG. 17B shows the results obtained for rat A7r5 VSMCs. It was found that the recombinant rat PARIS-4 suppressed the growth of VSMCs in both Sasco and A7r5 VSMCs. This constitutes direct proof of causality between PARIS-4 and growth suppression of VSMCs. In additional tests, 14 nM of PARIS-4 was found to inhibit VSMC growth (data how shown).

EXAMPLE 10

Immunohistochemical Detection of PARIS-4

Figure 18A:
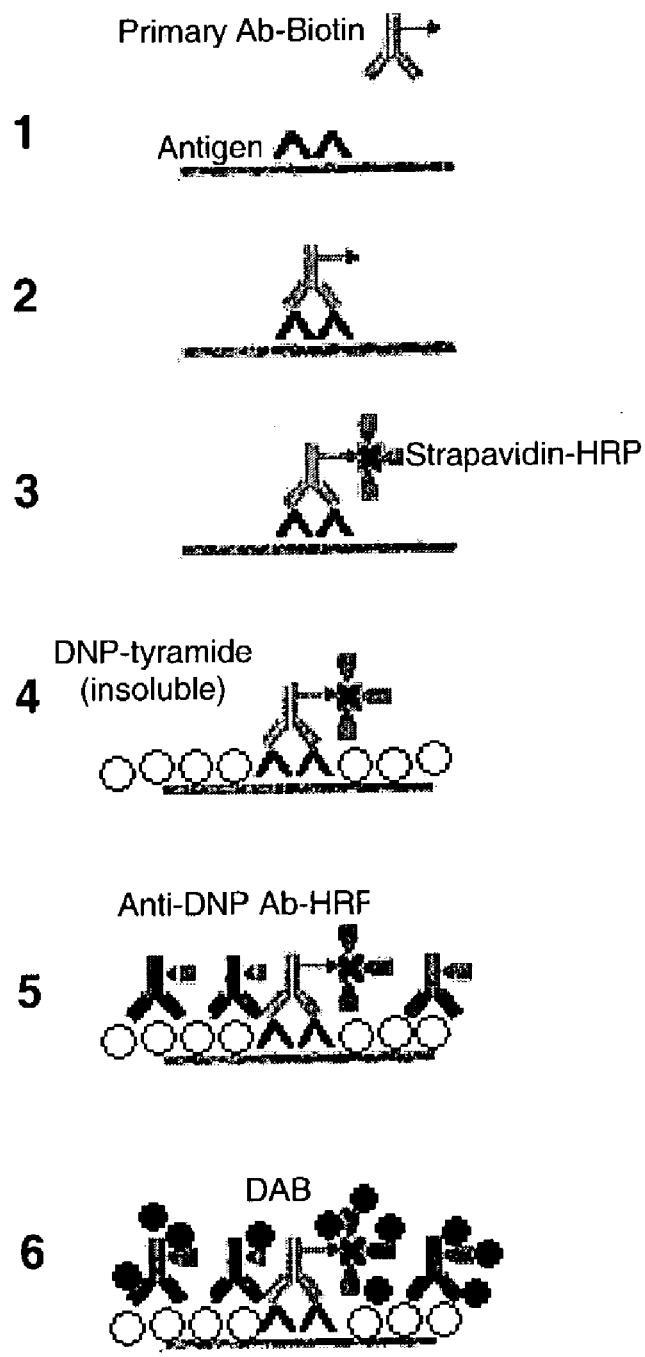
FIGS. 18A–D illustrate the immunohistochemical method employed and the results of immunohistochemical analysis of the neointima of balloon-injured rat carotid arteries to detect overexpression of PARIS-4.

Next, a new immunohistochemical (1HC) method was developed using tyramide signal amplification (TSA) to more effectively detect PARIS-4 in paraffin-embedded tissues. The results are shown in FIGS. 18A–D. The principle of TSA methods is illustrated in FIG. 18A. The open circles denote insoluble DNP-tyramide molecules; Solid circles denote 3,3'-diaminobenzidine (DAB). TSA staining was performed according to the manufacturer's instructions (NEN® Life Science Products; Boston, Mass.) with optimization for PARIS-4, as indicated. The following steps is conceptually illustrated in FIG. 18A.

(1)(2) After standard steps of deparaffinization, rehydration, and quenching of tissue peroxidase, tissue sections were incubated with biotinylated goat anti-rat PARIS-4 antibody (R&D Systems).

(3) After wash, tissue sections were incubated with streptavidin-horse radish peroxidase (HRP), followed by (4) application of dinitrophenyl (DNP) labeled tyramide. DNP-labeled tyramide was catalyzed to by HRP to form insoluble DNP depositions immediately adjacent to the immobilized HRP enzyme.

(5) These insolubly deposited DNP labels were detected by anti-DNP antibody conjugated to HRP.

(6) Finally, DAB, a substrate of HRP, was added. Because the added labels are deposited proximal to the initial immobilized HRP enzyme site, there is minimal loss in resolution.

Figure 18B:
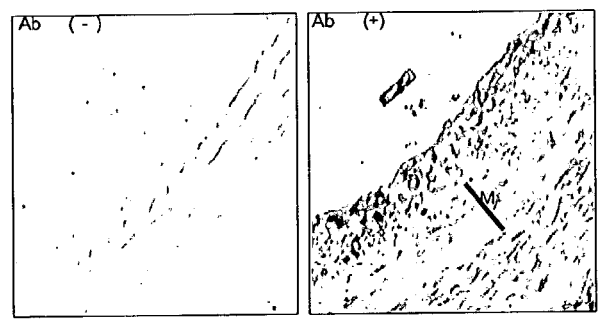

FIG. 18B shows photographically (×100) the TSA-enhanced immunohistochemistry of restenotic tissue. The restenotic tissue was stained using the TSA staining procedure described above. Ab(−) indicates no anti-PARIS-4 antibody (left panel). Ab(+) indicates Anti-PARIS-4 antibody present (right panel). M denotes media. In these photomicrographs it can be readily seen that the PARIS-4 signals are most intense in the neointima.

Figure 18C:
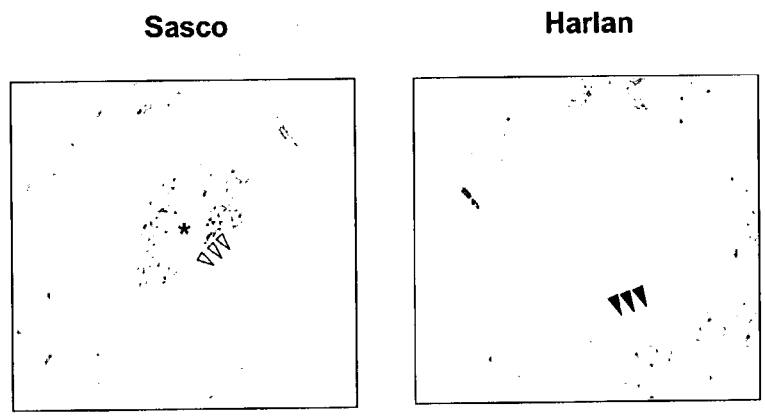

A comparison of PARIS-4 expression in Harlan and Sasco restenotic tissues is shown in FIG. 18C. Balloon-injured carotid arteries from Harlan (right panel) and Sasco (left panel) were stained using the methods above and presented in the lower magnification (×40). An asterisk denotes the clot formation within the lumen of the artery. Open arrows indicate the absence of PARIS-4 signal in Sasco neointima (left panel); closed arrows indicate the strong PARIS-4 signals seen in Harlan neointima (right panel).

Figure 18D:
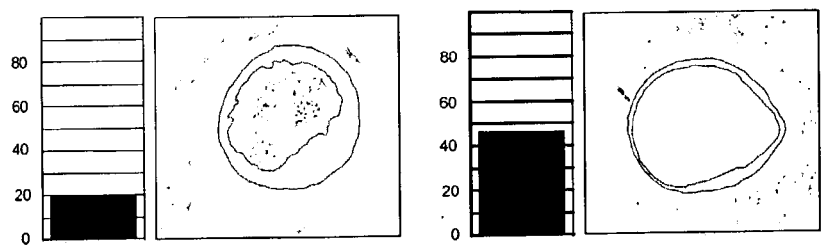

FIG. 18D shows the signal quantification. Using NIH "ImageJ" Software (NIH, Bethesda, Md.), DAB signal intensities were quantified and expressed in an arbitrary unit. DAB signal of Harlan neointima (right panel) was significantly higher (at least 2-fold) than that of Sasco neointima (left panel). Although a standard IHC method had yielded poor signal intensities in the past (data not shown) in these tissues, the present immunohistochemistry study using tyramide signal amplification (TSA) revealed definitively that PARIS-4 is overexpressed in the neointimal of balloon-injured rat carotid arteries in Harlan rats. Taken together with the data above (Examples 8 and 9), it is likely that PARIS-4, expressed more abundantly in Harlan neointimal VSMCs, is protective against neointimal proliferation and restenosis because PARIS-4 negatively regulates VSMC growth.

EXAMPLE 11

Quantification of PARIS-4 in Sera from Harlan and Sasco Rats

ELISA assays were next carried out on sera harvested from Harlan and Sasco SD rats (N=12), as described in Example 7. Intriguingly, Harlan sera contained a slightly higher but statistically not significant level of PARIS-4 than did Sasco sera (1102±302 and 1053±153 [ng/mL] for Harlan and Sasco, respectively, NS). In light of the fact that serum PARIS-4 concentrations are not different between Harlan and Sasco rats, it is suggested that PARIS-4 functions as a chemokine in local microenvironment rather than as a hormone in systemic environment.

EXAMPLE 12

Large-Scale Production of PARIS-4

Figure 19A:
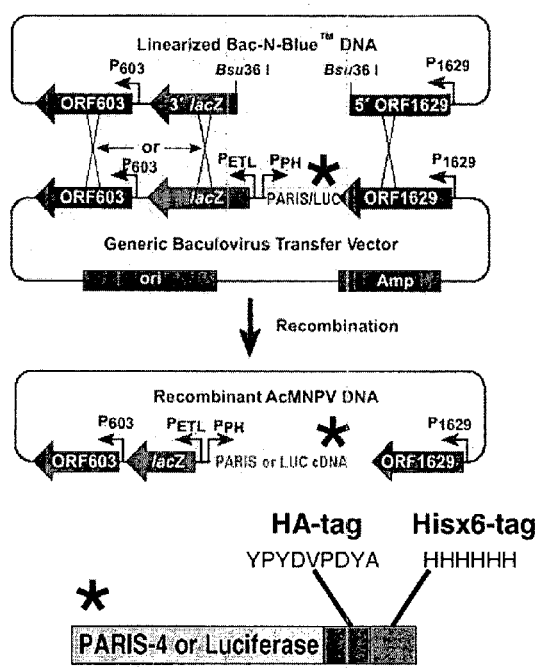
FIGS. 19A–C illustrate the feasibility of large scale production PARIS-4 protein production using baculovirus-Sf9 cell system.
Figure 19B:
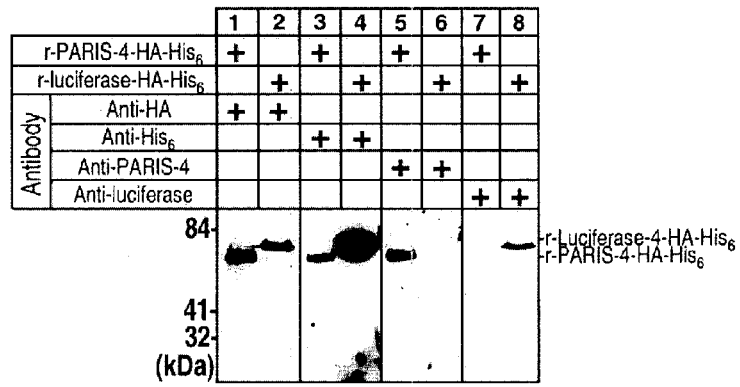
Figure 19C:
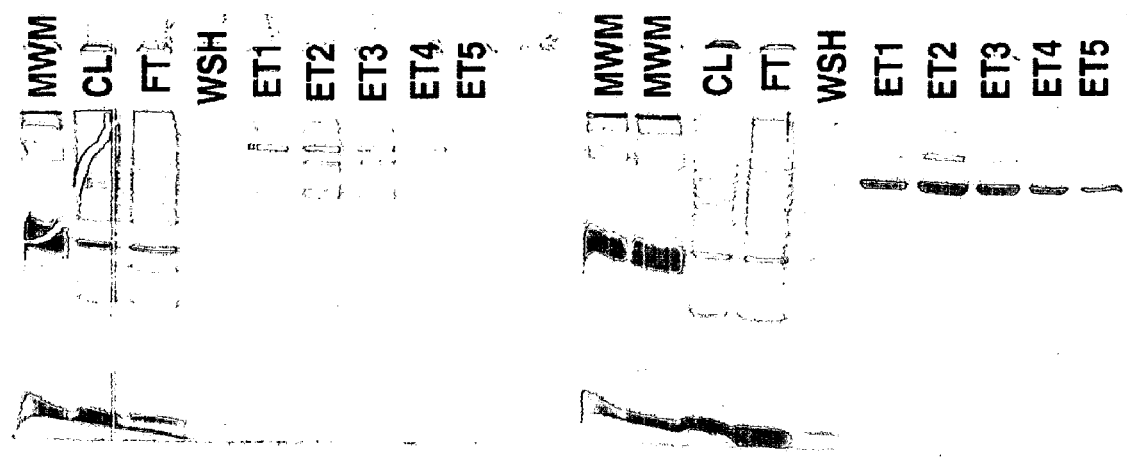

The feasibility of a large scale PARIS-4 protein production using baculovirus-Sf9 cell system was investigated. As illustrated in FIG. 19, a Baculovirus-Sf9 cell system yield a large amount of recombinant proteins. FIG. 19A is a schematic showing the production of recombinant AcMNPV-PARIS-4 and AcMNPV-luciferase (LUC). Asterisk denotes the detailed structure of the insert. Note that proteins are double-tagged with HA- and $His_{x6}$ tags. AcMNPV: *Autographa californica* nuclear polyhedrosis virus (baculovirus). The procedure was as follows: PARIS-4 cDNA was obtained by reverse transcription PCR (RT-PCR) using rat mRNA as a template with appropriate primer sets. The cDNAs of PARIS-4 and Luciferase were cloned into the pBlueBac4.5 vector, which had been modified in the inventors' laboratory to include HA- and $His_{x6}$ tags. These baculovirus transfer vectors were co-transfected with Invitrogen's linear Bac-N-Blue™ DNA into Sf21 insect cells to produce recombinant AcMNPVs. The recombinant viruses were plaque-purified and propagated. A small scale production and purification by Ni-NTA beads (Qiagen) were performed, using the lysates from Sf-9 cells infected with either AcMNPV-PARIS-4 or AcMNPV-LUC. The purified proteins were evaluated by Western blot analysis. Following antibodies were used; anti-HA (Roche), anti-His6 (Roche), anti-PARIS-4 (R&D Systems), and anti-luciferase (CalBiochem, San Diego, Calif.). FIG. 19B shows the Western blot analysis of proteins produced by recombinant AcMNPV-PARIS-4 and -LUC. In the figure, "r" indicates recombinant. FIG. 19C is a Coomassie blue stained gel electrophoresis of Ni-NTA™ (Quiagen, Inc., Valencia, Calif.) purified PARIS-4 and Luciferase (control) proteins. MWM: molecular weight marker, CL: cell lysate, FT: flow through, WSH: wash, ET1–5: elutions 1–5. The results suggest the successful production and purification of recombinant proteins. In ongoing work directed at scaling up protein production, it has been demonstrated that 645 µg of r-luciferase can be produced from $10^8/100$ mL of Sf-9 cells/media. More than 6 mg of protein production from 1000 mL of suspension culture is expected.

In light of all of the evidence presented in the foregoing Examples, it is concluded that PARIS-4 is one of the proteins that are produced by VSMCs and are more abundantly produced by Harlan VSMCs (restenosis resistant), and which are present in Harlan conditioned media (FIGS. 15A–C and 16). It is these proteins that are thought to inhibit the growth of VSMCs in vitro (FIGS. 8 and 17), and which inhibit the formation of neointima after balloon injury in vivo (FIGS. 18A–D). Because these data for PARIS-4 clearly validate the microarray analyses identifying the soluble negative growth inhibitors produced by the proliferating VSMCs, it is believed that PARISs 1–3, which were identified by the exact same microarray analyses, are also true negative growth regulators of VSMCs.

It is expected that additional PARIS proteins will be identified that share at least 24% amino acid identity with the above-identified rat PARISs, preferably sharing at least 40% identity, and still more preferably sharing about 60–100% amino acid identity. The counterpart proteins to the representative PARISs, in all mammals, are intended to be within the scope of the present invention. Furthermore, proteins having at least 40% homology to the above-identified rat amino acid sequences are also expected to provide at least some measure of cell growth inhibitory properties similar to those exemplified herein. Accordingly, all such proteins or polypeptides are considered to be PARISs. For example, homologous proteins may include a number of amino acid substitutions in which the differing amino acids have similar R-group substituents in terms of size, electrophilic character, charge, and the like. Some exemplary substitutions are listed in Table 6.

TABLE 6

| AMINO ACID SUBSTITUENTS FOR PARIS HOMOLOGS | |
|---|---|
| NATIVE AMINO ACID | AMINO ACID SUBSTITUTIONS |
| alanine | glycine; serine |
| arginine | lysine |
| asparagine | glutamine; histidine |
| aspartic acid | glutamic acid |
| cysteine | serine |
| glutamine | asparagine |
| glycine | alanine |
| histidine | asparagine; glutamine |
| isoleucine | leucine; valine |
| leucine | isoleucine; valine |
| lysine | arginine; glutamine; glutamic acid |
| methionine | leucine; tyrosine |
| serine | threonine |
| threonine | serine |
| tryptophan | tyrosine |
| tyrosine | tryptophan; phenylalanine |
| valine | isoleucine; leucine |

Some highly preferred PARIS proteins have the amino acid sequences of SEQ ID NOs.: 1–4 (human PARISs 1–4), and correspond to GenBank Accession No. Q15818 (PARIS-1), GenBank Accession No. NP_004855 (PARIS-2), GenBank Accession No. P78543 (PARIS-3), and GenBank Accession No. NP_002987 (PARIS-4), respectively, are listed in Table 7, along with all of their orthologs from representative animal models. The percent identity of orthologs of the rat PARISs 1–4 was estimated using the UniGene system of the National Center for Biotechnology Information of the National Institutes of Health. The UniGene system automatically partitions GenBank sequences into a non-redundant set of gene-oriented clusters. Each UniGene cluster contains sequences that represent a unique gene, as well as related information such as the tissue types in which the gene has been expressed and map location.[63]

plasma concentration of PARIS is 5–10 hold higher than normal serum concentrations of PARIS. The ideal methods of parenteral administration will be determined using animals first and then validated in human. Delivery of the purified PARIS(s) will be achieved by one of following methods: intravenous injection, subcutaneous injection, intraperitoneal injection, transcutaneous delivery, local delivery using PARIS-coated stents or infusion catheters; with/without liposomal or nanomolecular delivery systems. Suitable carriers for protein drugs are well known in the art.

TABLE 7

SELECTED MODEL ORGANISM PARIS PROTEIN SIMILARITIES

| | PARIS-1 | | PARIS-2 | | PARIS-3 | | PARIS-4 | |
|---|---|---|---|---|---|---|---|---|
| | GenBank Acc. No. | Identity[1] | GenBank Acc. No. | Identity[2] | GenBank Acc. No. | Identity[3] | GenBank Acc. No. | Identity[4] |
| *H. sapiens* | Q15818 | 95%/432 aa | NP_004855.1 | 100%/308 aa | P78543 | 92%/158 aa | NP_002987.1 | 67%/393 aa |
| *M. musculus* | Q62443 | 99%/432 aa | Q9Z0J7 | 58%/308 aa | Q04211 | 97%/158 aa | O35188 | 85%/393 aa |
| *R. norvegicus* | P47971 | 100%/432 aa | Q9Z0J7 | 59%/294 aa | A40443 | 100%/158 aa | O55145 | 100%/393 aa |
| *D. melanogaster* | | | P27091 | 31%/120 aa | | | | |
| *C. elegans* | | | NP_504709.1 | 29%/138 aa | | | NP_505150.1 | 24%/210 aa |

[1]UniGene Cluster Rn.54707 *R. norvegicus*
[2]UniGene Cluster Hs.296638 *H. sapiens*
[3]UniGene Cluster Rn.27923 *R. norvegicus*
[4]UniGene Cluster Rn.4106 *R. norvegicus*

EXAMPLE 13

Deterrence or Prevention of Post-Angioplasty Restenosis

PARISs produced in sterile, endotoxin-free environment using a standard CHO cell culture system will be administered to patients undergoing angioplasty procedures in order to suppress the growth of vascular smooth muscle cells and restenosis. It is believed that use of PARISs will be less expensive and more inclusive (i.e., they may be administered without special instruments or personnel) than conventional post-angioplasty restenosis treatments and preventatives.

Production of the PARIS protein will be carried out as follows: A PARIS-cDNA will be ligated into mammalian expression vector with the neomycin resistant gene that contains the sequence to allow the addition of polyhistidine tags at the C-terminus of the PARIS protein. CHO cells will be stably transfected with the vector and selected using G418. The clones that express PARIS most abundantly will be selected. Cells will then be adjusted to serum-free medium system. PARIS will be secreted into the media since it contains a secretion marker. PARIS will then be purified using the metal ion chromatography with Ni-NTA beads to near homogeneity. To achieve the further purity, the purified protein will further be purified by ion-exchange chromatography. All the procedures will be completed under sterile and endotoxin-free conditions. Purified proteins will be tested for the endotoxin contents.

An appropriate PARIS protein dose will be determined as follows: Various amounts of proteins will be parenterally administered first to animals (then after completion of full animal studies to human) and multiple blood samplings will be performed over time (ex. 1, 2, 4, 8, and 24 hrs). The samples will be then evaluated by ELISA methods described earlier. The ideal dosing of the PARIS would be such that The PARISs may be coated onto stents using known techniques that have been previously employed with other drug-eluting stents.

It is also envisioned that in a certain circumstance, the combination of two or more PARISs will be administered to enhance the anti-proliferative effect of PARISs. PARISs can be used together with drug-coated stents, plain stents, and any other interventional methods used in current and future percutaneous coronary interventions.

EXAMPLE 14

Treatment of Post-Angioplasty Restenosis

For the treatment of post-angioplasty or in stent restenosis, PARISs will be delivered through routes in Example 13, before, during or after the PCI to address the restenosis, including stent (coated or noncoated) implantation, brachytherapy, and any other current and future PCI methods appropriate for the condition. Advantageously, a stent deployed in conjunction with conventional PCI methods to address restenosis may be readily coated with PARISs using substantially known techniques.

EXAMPLE 15

Delaying or Arresting Progression of Atherosclerosis

Purified PARISs are administered to patients with atherosclerosis in order to suppress the growth of vascular smooth muscle cells at the site of an atherosclerotic lesion. PARISs can be subcutaneously injected into patients who are at high risk for developing premature atherosclerosis, injected into patients who have already had atherosclerosis with or without its long term complications (e.g., CAD, MI, angina, etc.). Patients who are expected to benefit from long term PARIS treatment include those with cardiac transplantation (for deterring or preventing transplantation atherosclerosis) and those patients receiving coronary artery bypass grafts (CABG), for deterrence or prevention of graft failure. Systemic or subcutaneous administration of PARISs is expected to offer advantages for treatment of small vessels, where conventional drug-eluting stents are not appropriate.

EXAMPLE 16

Deterrence, Prevention and Treatment of Other Smooth Muscle Cell-Related Proliferative Disorders This unique group of proteins (PARISs) are also believed to hold promise for treating a variety of other proliferative disorders. Although PARISs were originally identified as the proteins produced by VSMCs for inhibiting the growth of VSMCs, it is likely that PARISs have similar biological activity (e.g., cell growth inhibitory effects) on normal and abnormal cells other than vascular smooth muscle cells. For example, postsurgical keloid formation involves not only VSMCs but also fibroblasts and other cell types. PARISs may block keloid formation through the negative growth regulation over all of these cells. Furthermore, proliferative diabetic retinopathy represents the formation of neo-arteries in the retina, which are fragile, and tends to bleed. PARISs may be used to prevent such neo-artery formation. Certain tumors, such as hemangioma, rhabdomyoma, rhabdomyosarcoma, fibromyoma of the uterus, and other vascular and muscular tumors, either benign or malignant, may be effectively treated by PARISs. Furthermore, tumors and cancers that do not contain smooth muscle components may well respond to PARISs in a higher dose. In summary, PARISs may prove useful in any type of malignancy in humans.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. For example, biologically active portions of the above-described PARIS proteins are also contemplated as part of the present invention. Such bioactive polypeptides may serve as receptor ligation regions for a native PARIS, or may correspond to a region of a PARIS that participates in protein-protein interaction with another protein, which regulates the activity of the PARIS. Accordingly, the scope of protection is not limited by the description set out above and is intended to include all equivalents of the subject matter described herein. The disclosures of all patents, patent applications and publications cited herein are hereby specifically incorporated herein by reference, to the extent that they provide materials, methods or other details supplementary to those set forth herein.

REFERENCES

1. Sigwart U., Puel J., Mirkovitch V., et al., *Intravascular stents to prevent occlusion and restenosis after transluminal angioplasty*, N. Engl. J. Med. 1987 316:701–6.
2. Erbel R., Haude M., Hopp H. W., et al., *Coronary-artery stenting compared with balloon angioplasty for restenosis after initial balloon angioplasty*, Restenosis Stent Study Group, N Engl J. Med. 1998;339:1672–8.
3. Kearney M., Pieczek A., Haley L., et al., *Histopathology of in-stent restenosis in patients with peripheral artery disease*, Circulation. 1997;95:1998–2002.
4. vom Dahl J., Dietz U., Haager P. K., et al., *Rotational atherectomy does not reduce recurrent in-stent restenosis: results of the angioplasty versus rotational atherectomy for treatment of diffuse in-stent restenosis trial (ARTIST)*, Circulation. 2002;105:583–8.
5. Leon M. B., Teirstein P. S., Moses J. W., et al., *Localized intracoronary gamma-radiation therapy to inhibit the recurrence of restenosis after stenting*, N. Engl. J. Med. 2001;344:250–6.
6. Tardif J. C., Cote G., Lesperance J., et al., *Probucol and multivitamins in the prevention of restenosis after coronary angioplasty*, Multivitamins and Probucol Study Group, N. Engl J. Med. 1997;337:365–72.
7. Maresta A., Balducelli M., Cantini L., et al., *Trapidil (triazolopyrimidine), a platelet-derived growth factor antagonist, reduces restenosis after percutaneous transluminal coronary angioplasty. Results of the randomized, double-blind STARC study. Studio Trapidil versus Aspirin nella Restenosi Coronarica*, Circulation. 1994;90:2710–5.
8. Tsuchikane E., Fukuhara A., Kobayashi T., et al., *Impact of cilostazol on restenosis after percutaneous coronary balloon angioplasty*, Circulation. 1999;100:21–6.
9. Dehmer G. J., Popma J. J., van den Berg E. K., et al., *Reduction in the rate of early restenosis after coronary angioplasty by a diet supplemented with n-3 fatty acids*, N. Engl. J. Med. 1988;319:733–40.
10. Schnyder G., Roffi M., Pin R., et al., *Decreased rate of coronary restenosis after lowering of plasma homocysteine levels*, N. Engl. J. Med. 2001;345:1593–600.
11. Fischman D. L., Leon M. B., Baim D. S., et al., *A randomized comparison of coronary-stent placement and balloon angioplasty in the treatment of coronary artery disease. Stent Restenosis Study Investigators*, N. Engl. J. Med. 1994;331:496–501.
12. Teirstein P. S., Massullo V., Jani S., et al., *Catheter-based radiotherapy to inhibit restenosis after coronary stenting*, N Engl J. Med. 1997;336:1697–703.
13. Verin V., Popowski Y., de Bruyne B., et al., *Endoluminal beta-radiation therapy for the prevention of coronary restenosis after balloon angioplasty*, The Dose-Finding Study Group. N Engl J. Med. 2001;344:243–9.
14. Cannon R. O., 3rd. *Restenosis after angioplasty*, N Engl J. Med. 2002;346:1182–3.
15. Califf R. M., *Restenosis: the cost to society*, Am Heart J. 1995;130:680–4.
16. Clowes A. W., Reidy M. A., Clowes M. M., *Kinetics of cellular proliferation after arterial injury. I. Smooth muscle growth in the absence of endothelium*, Lab Invest. 1983;49:327–33.
17. Klinger M. M., MacCarter G. D., Boozer C. N., *Body weight and composition in the Sprague Dawley rat: comparison of three outbred sources*, Lab Anim Sci. 1996;46:67–70.
18. Knight E., Bryant S., Keenan C., et al., *Two year evaluation of clinical parameters and pathology in Sprague-Dawley ratsfrom different suppliers*, Toxicologist. 1994;14:303–314.
19. Fuller D. D., Baker T. L., Behan M., et al., *Expression of hypoglossal long-term facilitation differs between substrains of Sprague-Dawley rat*, Physiol Genomics. 2001; 4:175–81.
20. Sluka K. A., Westlund K. N., *Spinal projections of the locus coeruleus and the nucleus subcoeruleus in the Harlan and the Sasco Sprague-Dawley rat*, Brain Res. 1992;579:67–73.

21. West W. L., Yeomans D. C., Proudfit H. K., *The function of noradrenergic neurons in mediating antinociception induced by electrical stimulation of the locus coeruleus in two different sources of Sprague-Dawley rats*, Brain Res. 1993;626:127–35.
22. Turnbull A. V., Rivier C. L., *Sprague-Dawley rats obtained from different vendors exhibit distinct adrenocorticotropin responses to inflammatory stimuli*, Neuroendocrinology. 1999;70:186–95.
23. Li C., Wong W. H., *Model-based analysis of oligonucleotide arrays: expression index computation and outlier detection*, Proc Natl Acad Sci USA. 2001;98:31–6.
24. Cheng Y, Austin SC, Rocca B, et al. *Role of prostacyclin in the cardiovascular response to thromboxane A2*. Science. 2002;296:539–41.
25. Cipollone F, Marini M, Fazia M, et al. *Elevated circulating levels of monocyte chemoattractant protein-1 in patients with restenosis after coronary angioplasty*. Arterioscler Thromb Vasc Biol. 2001;21:327–34.
26. Oguchi S, Dimayuga P, Zhu J, et al. Monoclonal antibody against vascular cell adhesion molecule-1 inhibits neointimal formation after periadventitial carotid artery injury in genetically hypercholesterolemic mice. Arterioscler Thromb Vasc Biol. 2000;20:1729–36.
27. Huckle W R, Drag M D, Acker W R, et al. Effects of subtype-selective and balanced angiotensin II receptor antagonists in a porcine coronary artery model of vascular restenosis. Circulation. 1996;93:1009–19.
28. Viswanathan M, Stromberg C, Seltzer A, et al. Balloon angioplasty enhances the expression of angiotensin II AT1 receptors in neointima of rat aorta. J Clin Invest. 1992; 90:1707–12.
29. Asada Y, Hara S, Tsuneyoshi A, et al. Fibrin-rich and platelet-rich thrombus formation on neointima: recombinant tissue factor pathway inhibitor prevents fibrin formation and neointimal development following repeated balloon injury of rabbit aorta. Thromb Haemost. 1998; 80:506–11.
30. Atsuchi N, Nishida T, Marutsuka K, et al. Combination of a brief irrigation with tissue factor pathway inhibitor (TFPI) and adenovirus-mediated local TFPI gene transfer additively reduces neointima formation in balloon-injured rabbit carotid arteries. Circulation. 2001;103:570–5.
31. Hasenstab D, Lea H, Hart CE, et al. Tissue factor overexpression in rat arterial neointima models thrombosis and progression of advanced atherosclerosis. Circulation. 2000; 101:2651–7.
32. Shigematsu K, Koyama H, Olson NE, et al. Phosphatidylinositol 3-kinase signaling is important for smooth muscle cell replication after arterial injury. Arterioscler Thromb Vasc Biol. 2000;20:2373–8.
33. Imanaka-Yoshida K, Matsuura R, Isaka N, et al. Serial extracellular matrix changes in neointimal lesions of human coronary artery after percutaneous transluminal coronary angioplasty: clinical significance of early tenascin-C expression. Virchows Arch. 2001;439:185–90.
34. Nikol S, Isner J M, Pickering J G, et al. Expression of transforming growth factor-beta 1 is increased in human vascular restenosis lesions. J Clin Invest. 1992;90:1582–92.
35. Schmidt A M, Stern D M. Chemokines on the rise: mcp-1 and restenosis. Arterioscler Thromb Vasc Biol. 2001;21: 297–9.
36. Schlimgen A K, Helms J A, Vogel H, et al. Neuronal pentraxin, a secreted protein with homology to acute phase proteins of the immune system. Neuron. 1995; 14:519–26.
37. Hsu Y C, Perin M S. Human neuronal pentraxin II (NPTX2): conservation, genomic structure, and chromosomal localization. Genomics. 1995;28:220–7.
38. Kirkpatrick L L, Matzuk M M, Dodds D C, et al. Biochemical interactions of the neuronal pentraxins. Neuronal pentraxin (NP) receptor binds to taipoxin and taipoxin-associated calcium-binding protein 49 via NP1 and NP2. J. Biol. Chem. 2000;275:17786–92.
39. DeGregorio-Rocasolano N, Gasull T, Trullas R. Overexpression of neuronal pentraxin 1 is involved in neuronal death evoked by low K(+) in cerebellar granule cells. J. Biol. Chem. 2001;276:796–803.
40. Bootcov M R, Bauskin A R, Valenzuela S M, et al. MIC-1, a novel macrophage inhibitory cytokine, is a divergent member of the TGF-beta superfamily. Proc Natl Acad Sci USA. 1997;94:11514–9.
41. Bauskin A R, Zhang H P, Fairlie W D, et al. The propeptide of macrophage inhibitory cytokine (MIC-1), a TGF-beta superfamily member, acts as a quality control determinant for correctly folded MIC-1. Embo J. 2000; 19:2212–20.
42. Shull M M, Ormsby I, Kier A B, et al. Targeted disruption of the mouse transforming growth factor-beta 1 gene results in multifocal inflammatory disease. Nature. 1992;359:693–9.
43. Bradbury A, Possenti R, Shooter E M, et al. Molecular cloning of PC3, a putatively secreted protein whose mRNA is induced by nerve growth factor and depolarization. Proc Natl Acad Sci USA. 1991;88:3353–7.
44. Lin W J, Chang Y F, Wang W L, et al. Mitogen-stimulated TIS21 protein interacts with a protein-kinase-Calpha-binding protein rPICK1. Biochem J. 2001;354: 635–43.
45. Lin W J, Gary J D, Yang M C, et al. The mammalian immediate-early TIS21 protein and the leukemia-associated BTG1 protein interact with a protein-arginine N-methyltransferase. J. Biol. Chem. 1996;271:15034–44.
46. Prevot D, Morel A P, Voeltzel T, et al. Relationships of the antiproliferative proteins BTG1 and BTG2 with CAF1, the human homolog of a component of the yeast CCR4 transcriptional complex: involvement in estrogen receptor alpha signaling pathway. J. Biol. Chem. 2001; 276:9640–8.
47. Rouault J P, Falette N, Guehenneux F, et al. Identification of BTG2, an antiproliferative p53-dependent component of the DNA damage cellular response pathway. Nat Genet. 1996; 14:482–6.
48. Fong A M, Erickson H P, Zachariah J P, et al. Ultrastructure and function of the fractalkine mucin domain in CX(3)C chemokine domain presentation. J. Biol. Chem. 2000;275:3781–6.
49. Imai T, Hieshima K, Haskell C, et al. Identification and molecular characterization of fractalkine receptor CX3CR1, which mediates both leukocyte migration and adhesion. Cell. 1997;91:521–30.
50. Maciejewski-Lenoir D, Chen S, Feng L, et al. Characterization of fractalkine in rat brain cells: migratory and activation signals for CX3CR-1-expressing microglia. J. Immunol. 1999;163:1628–35.
51. Feng L, Chen S, Garcia GE, et al. Prevention of crescentic glomerulonephritis by immunoneutralization of the fractalkine receptor CX3CR1 rapid communication. Kidney Int. 1999;56:612–20.
52. Zujovic V, Schussler N, Jourdain D, et al. In vivo neutralization of endogenous brain fractalkine increases hippocampal TNFalpha and 8-isoprostane production induced by intracerebroventricular injection of LPS. *J Neuroimmunol.* 2001; 115:135–43.

53. Ludwig A, Berkhout T, Moores K, et al. Fractalkine is expressed by smooth muscle cells in response to IFN-gamma and TNF-alpha and is modulated by metalloproteinase activity. *J. Immunol.* 2002;168:604–12.

54. Nielsen H, Engelbrecht J, Brunak S, et al. Identification of prokaryotic and eukaryotic signal peptides and prediction of their cleavage sites. *Protein Eng.* 1997;10:1–6.

55. Morice M-C, Serruys P, Sousa E, et al. A randomized comparison of a sirolimus-eluting stent with a standard stent for coronary revascularization. *N Engl J. Med.* 2002;346:1773–1780.

56. Klinger M M, MacCarter G D, Boozer C N. Body weight and composition in the Sprague Dawley rat: comparison of three outbred sources. *Lab Anim Sci.* 1996;46:67–70.

57. Knight E, Bryant S, Keenan C, Kimball J, Barrett D. Two year evaluation of clinical parameters and pathology in Sprague-Dawley rats from different suppliers. *Toxicologist.* 1994;14:303–314.

58. Fuller D D, Baker T L, Behan M, Mitchell G S. Expression of hypoglossal long-term facilitation differs between substrains of Sprague-Dawley rat. *Physiol Genomics.* 2001;4:175–181.

59. Sluka K A, Westlund K N. Spinal projections of the locus coeruleus and the nucleus subcoeruleus in the Harlan and the Sasco Sprague-Dawley rat. *Brain Res.* 1992;579:67–73.

60. West W L, Yeomans D C, Proudfit H K. The function of noradrenergic neurons in mediating antinociception induced by electrical stimulation of the locus coeruleus in two different sources of Sprague-Dawley rats. *Brain Res.* 1993;626:127–135.

61. Turnbull A V, Rivier C L. Sprague-Dawley rats obtained from different vendors exhibit distinct adrenocorticotropin responses to inflammatory stimuli. *Neuroendocrinology.* 1999;70:186–195

62. Reczko M., Staub E, Fiziev P, et al. Finding Signal Peptides in Human Protein Sequences using Recurrent Neural Networks. In R. Guigo and D. Gusfield (eds.): Algorithms in Bioinformatics, Proceedings of the 2nd Int. Workshop WABI 2002, Rome, Italy, Sep. 16–21, 2002. Lecture Notes in Computer Science, Springer, Volume 2452, pp. 60–67.

63. *NCBI News*, August 1997. National Center for Biotechnology Information, National Institutes of Health.

64. Nielsen H, Engelbrecht J, Brunak S, et al. Identification of prokaryotic and eukaryotic signal peptides and prediction of their cleavage sites. *Protein Eng.* 1997;10:1–6.

65. Bradbury A, Possenti R, Shooter E M, et al. Molecular cloning of PC3, a putatively secreted protein whose mRNA is induced by nerve growth factor and depolarization. *Proc Natl Acad Sci USA.* 1991;88:3353–7.

What is claimed is:

1. A method of inhibiting vascular smooth muscle cell proliferation comprising contacting said cell with an inhibitor comprising PARIS-4, whereby proliferation of said smooth muscle cell is inhibited.

2. The method of claim 1, wherein said contacting comprises administering said inhibitor to a patient at risk of atherosclerosis progression, to suppress the proliferation of vascular smooth muscle cells in said patient, whereby the risk of atherosclerosis progression in the patient is reduced.

3. The method of claim 1 wherein said PARIS-4 comprises the extracellular domain of SEQ. ID NO: 4.

4. A method of inhibiting vascular smooth muscle cell proliferation comprising contacting said cell with an inhibitor comprising at least one protein or polypeptide selected from the group consisting of the extracellularly expressed portion of a fractalkine homolog selected from the group consisting of *Homo sapiens* fractalkine, *Mus musculus* fractalkine, *Rattus norvegicus* fractalkine and *Caenorhabditis elegans* fractalkine, whereby proliferation of said smooth muscle cell is inhibited.

5. A method of deterring or preventing restenosis caused by vascular smooth muscle cell proliferation comprising carrying out the method of claim 4 wherein said contacting comprises administering to a patient at risk of restenosis an amount of said inhibitor effective to inhibit vascular smooth muscle cell proliferation resulting in deterrence or prevention of said restenosis.

6. The method of claim 5 wherein said patient is undergoing an angioplasty procedure and said administering comprises administering an effective amount of said inhibitor to said patient before, during or after an angioplasty procedure, to deter or prevent said restenosis.

7. The method of claim 6 wherein said angioplasty procedure includes placement of a stent at an angioplasty site in said patient.

8. The method of claim 7 wherein said stent is a drug-eluting stent capable of releasing said inhibitor in situ.

9. The method of claim 6 wherein said administering includes delivering said inhibitor to an angioplasty site in said patient.

* * * * *

```
                        SEQUENCE LISTING

<160> NUMBER OF SEQ ID NOS: 4

<210> SEQ ID NO 1
<211> LENGTH: 429
<212> TYPE: PRT
<213> ORGANISM: Homo sapiens
<300> PUBLICATION INFORMATION:
<308> DATABASE ACCESSION NUMBER: GenBank / Q15818
<309> DATABASE ENTRY DATE: 2001-10-16
<313> RELEVANT RESIDUES: (1)..(429)

<400> SEQUENCE: 1

Met Pro Ala Gly Arg Ala Arg Thr Cys Ala Leu Leu Ala Leu Cys Leu
1               5                   10                  15

Leu Gly Pro Gln Asp Phe Gly Pro Thr Arg Phe Ile Cys Thr Ser Val
                20                  25                  30

Pro Val Asp Ala Asp Met Cys Ala Ala Ser Val Ala Ala Gly Gly Ala
            35                  40                  45

Glu Glu Leu Arg Ser Ser Asn Val Leu Gln Leu Arg Glu Thr Val Leu
    50                  55                  60

Gln Gln Lys Glu Thr Ile Leu Ser Gln Lys Glu Thr Ile Arg Glu Leu
65                  70                  75                  80

Thr Ala Lys Leu Gly Arg Cys Glu Ser Gln Ser Thr Leu Asp Pro Gly
                85                  90                  95

Ala Gly Glu Ala Arg Ala Gly Gly Arg Lys Gln Pro Gly Ser Gly
            100                 105                 110

Lys Asn Thr Met Gly Asp Leu Ser Arg Thr Pro Ala Ala Glu Thr Leu
            115                 120                 125

Ser Gln Leu Gly Gln Thr Leu Gln Ser Leu Lys Thr Arg Leu Glu Asn
130                 135                 140
```

-continued

```
Leu Glu Gln Tyr Ser Arg Leu Asn Ser Ser Gln Thr Asn Ser Leu
145                 150                 155                 160

Lys Asp Leu Leu Gln Ser Lys Ile Asp Glu Leu Glu Arg Gln Val Leu
                165                 170                 175

Ser Arg Val Asn Thr Leu Glu Glu Gly Lys Gly Gly Pro Lys Asn Asp
            180                 185                 190

Thr Glu Glu Arg Val Lys Ile Glu Thr Ala Leu Thr Ser Leu His Gln
        195                 200                 205

Arg Ile Ser Glu Leu Glu Lys Gly Gln Lys Asp Asn Arg Pro Gly Asp
    210                 215                 220

Lys Phe Gln Leu Thr Phe Pro Leu Arg Thr Asn Tyr Met Tyr Ala Lys
225                 230                 235                 240

Val Lys Lys Ser Leu Pro Glu Met Tyr Ala Phe Thr Val Cys Met Trp
                245                 250                 255

Leu Lys Ser Ser Ala Thr Pro Gly Val Gly Thr Pro Phe Ser Tyr Ala
            260                 265                 270

Val Pro Gly Gln Ala Asn Glu Leu Val Leu Ile Glu Trp Gly Asn Asn
        275                 280                 285

Pro Met Glu Ile Leu Ile Asn Asp Lys Val Ala Lys Leu Pro Phe Val
    290                 295                 300

Ile Asn Asp Gly Lys Trp His His Ile Cys Val Thr Trp Thr Thr Arg
305                 310                 315                 320

Asp Gly Val Glu Ala Tyr Gln Asp Gly Thr Gln Gly Ser Gly Glu
                325                 330                 335

Asn Leu Ala Pro Tyr His Pro Ile Lys Pro Gln Gly Val Leu Val Leu
            340                 345                 350

Gly Gln Glu Gln Asp Thr Leu Gly Gly Gly Phe Asp Ala Thr Gln Ala
        355                 360                 365

Phe Val Gly Glu Leu Ala His Phe Asn Ile Trp Asp Arg Lys Leu Thr
    370                 375                 380

Pro Gly Glu Val Tyr Asn Leu Ala Thr Cys Ser Thr Lys Ala Leu Ser
385                 390                 395                 400

Gly Asn Val Ile Ala Trp Ala Glu Ser His Ile Glu Ile Tyr Gly Gly
                405                 410                 415

Ala Thr Lys Trp Thr Phe Glu Ala Cys Arg Gln Ile Asn
            420                 425
```

<210> SEQ ID NO 2
<211> LENGTH: 308
<212> TYPE: PRT
<213> ORGANISM: Homo sapiens
<300> PUBLICATION INFORMATION:
<308> DATABASE ACCESSION NUMBER: GenBank / NP_004855
<309> DATABASE ENTRY DATE: 2003-04-07
<313> RELEVANT RESIDUES: (1)..(308)

<400> SEQUENCE: 2

```
Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
                20                  25                  30

Ala Glu Ala Ser Arg Ala Ser Phe Pro Gly Pro Ser Glu Leu His Ser
            35                  40                  45

Glu Asp Ser Arg Phe Arg Glu Leu Arg Lys Arg Tyr Glu Asp Leu Leu
        50                  55                  60

Thr Arg Leu Arg Ala Asn Gln Ser Trp Glu Asp Ser Asn Thr Asp Leu
```

-continued

```
            65                  70                  75                  80
Val Pro Ala Pro Ala Arg Ile Leu Thr Pro Glu Val Arg Leu Gly
                 85                  90                  95

Ser Gly Gly His Leu His Leu Arg Ile Ser Arg Ala Ala Leu Pro Glu
                100                 105                 110

Gly Leu Pro Glu Ala Ser Arg Leu His Arg Ala Leu Phe Arg Leu Ser
            115                 120                 125

Pro Thr Ala Ser Arg Ser Trp Asp Val Thr Arg Pro Leu Arg Arg Gln
        130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ala
                165                 170                 175

Arg Pro Gln Leu Glu Leu His Leu Arg Pro Gln Ala Ala Arg Gly Arg
                180                 185                 190

Arg Arg Ala Arg Ala Arg Asn Gly Asp Asp Cys Pro Leu Gly Pro Gly
                195                 200                 205

Arg Cys Cys Arg Leu His Thr Val Arg Ala Ser Leu Glu Asp Leu Gly
        210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Glu Pro Ala Pro
                260                 265                 270

Cys Cys Val Pro Ala Ser Tyr Asn Pro Met Val Leu Ile Gln Lys Thr
                275                 280                 285

Asp Thr Gly Val Ser Leu Gln Thr Tyr Asp Asp Leu Leu Ala Lys Asp
        290                 295                 300

Cys His Cys Ile
305
```

```
<210> SEQ ID NO 3
<211> LENGTH: 158
<212> TYPE: PRT
<213> ORGANISM: Homo sapiens
<300> PUBLICATION INFORMATION:
<308> DATABASE ACCESSION NUMBER: GenBank / P78543
<309> DATABASE ENTRY DATE: 2002-06-15
<313> RELEVANT RESIDUES: (1)..(158)

<400> SEQUENCE: 3

Met Ser His Gly Lys Gly Thr Asp Met Leu Pro Glu Ile Ala Ala Ala
1               5                   10                  15

Val Gly Phe Leu Ser Ser Leu Leu Arg Thr Arg Gly Cys Val Ser Glu
                20                  25                  30

Gln Arg Leu Lys Val Phe Ser Gly Ala Leu Gln Glu Ala Leu Thr Glu
            35                  40                  45

His Tyr Lys His Trp Phe Pro Glu Lys Pro Ser Lys Gly Ser Gly
        50                  55                  60

Tyr Arg Cys Ile Arg Ile Asn His Lys Met Asp Pro Ile Ile Ser Arg
65                  70                  75                  80

Val Ala Ser Gln Ile Gly Leu Ser Gln Pro Gln Leu His Gln Leu Leu
                85                  90                  95

Pro Ser Glu Leu Thr Leu Trp Val Asp Pro Tyr Glu Val Ser Tyr Arg
                100                 105                 110
```

-continued

```
Ile Gly Glu Asp Gly Ser Ile Cys Val Leu Tyr Glu Glu Ala Pro Leu
            115                 120                 125
Ala Ala Ser Cys Gly Leu Leu Thr Cys Lys Asn Gln Val Leu Leu Gly
        130                 135                 140
Arg Ser Ser Pro Ser Lys Asn Tyr Val Met Ala Val Ser Ser
145                 150                 155

<210> SEQ ID NO 4
<211> LENGTH: 397
<212> TYPE: PRT
<213> ORGANISM: Homo sapiens
<300> PUBLICATION INFORMATION:
<308> DATABASE ACCESSION NUMBER: GenBank / NP_002987
<309> DATABASE ENTRY DATE: 2003-04-07
<313> RELEVANT RESIDUES: (1)..(397)

<400> SEQUENCE: 4

Met Ala Pro Ile Ser Leu Ser Trp Leu Leu Arg Leu Ala Thr Phe Cys
1               5                   10                  15
His Leu Thr Val Leu Leu Ala Gly Gln His His Gly Val Thr Lys Cys
            20                  25                  30
Asn Ile Thr Cys Ser Lys Met Thr Ser Lys Ile Pro Val Ala Leu Leu
        35                  40                  45
Ile His Tyr Gln Gln Asn Gln Ala Ser Cys Gly Lys Arg Ala Ile Ile
    50                  55                  60
Leu Glu Thr Arg Gln His Arg Leu Phe Cys Ala Asp Pro Lys Glu Gln
65                  70                  75                  80
Trp Val Lys Asp Ala Met Gln His Leu Asp Arg Gln Ala Ala Ala Leu
                85                  90                  95
Thr Arg Asn Gly Gly Thr Phe Glu Lys Gln Ile Gly Glu Val Lys Pro
            100                 105                 110
Arg Thr Thr Pro Ala Ala Gly Gly Met Asp Glu Ser Val Val Leu Glu
        115                 120                 125
Pro Glu Ala Thr Gly Glu Ser Ser Ser Leu Glu Pro Thr Pro Ser Ser
    130                 135                 140
Gln Glu Ala Gln Arg Ala Leu Gly Thr Ser Pro Glu Leu Pro Thr Gly
145                 150                 155                 160
Val Thr Gly Ser Ser Gly Thr Arg Leu Pro Pro Thr Pro Lys Ala Gln
                165                 170                 175
Asp Gly Gly Pro Val Gly Thr Glu Leu Phe Arg Val Pro Pro Val Ser
            180                 185                 190
Thr Ala Ala Thr Trp Gln Ser Ser Ala Pro His Gln Pro Gly Pro Ser
        195                 200                 205
Leu Trp Ala Glu Ala Lys Thr Ser Glu Ala Pro Ser Thr Gln Asp Pro
    210                 215                 220
Ser Thr Gln Ala Ser Thr Ala Ser Ser Pro Ala Pro Glu Glu Asn Ala
225                 230                 235                 240
Pro Ser Glu Gly Gln Arg Val Trp Gly Gln Gly Gln Ser Pro Arg Pro
                245                 250                 255
Glu Asn Ser Leu Glu Arg Glu Glu Met Gly Pro Val Pro Ala His Thr
            260                 265                 270
Asp Ala Phe Gln Asp Trp Gly Pro Gly Ser Met Ala His Val Ser Val
        275                 280                 285
Val Pro Val Ser Ser Glu Gly Thr Pro Ser Arg Glu Pro Val Ala Ser
    290                 295                 300
```

-continued

```
Gly Ser Trp Thr Pro Lys Ala Glu Glu Pro Ile His Ala Thr Met Asp
305                 310                 315                 320

Pro Gln Arg Leu Gly Val Leu Ile Thr Pro Val Pro Asp Ala Gln Ala
            325                 330                 335

Ala Thr Arg Arg Gln Ala Val Gly Leu Leu Ala Phe Leu Gly Leu Leu
            340                 345                 350

Phe Cys Leu Gly Val Ala Met Phe Thr Tyr Gln Ser Leu Gln Gly Cys
        355                 360                 365

Pro Arg Lys Met Ala Gly Glu Met Ala Glu Gly Leu Arg Tyr Ile Pro
        370                 375                 380

Arg Ser Cys Gly Ser Asn Ser Tyr Val Leu Val Pro Val
385                 390                 395
```